(12) United States Patent
Lippard et al.

(10) Patent No.: US 8,729,286 B2
(45) Date of Patent: May 20, 2014

(54) PLATINUM COMPOUNDS AS TREATMENT FOR CANCERS, AND RELATED METHODS, KITS, AND COMPOSITIONS

(75) Inventors: Stephen J. Lippard, Cambridge, MA (US); Justin J. Wilson, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/468,477

(22) Filed: May 10, 2012

(65) Prior Publication Data

US 2013/0303606 A1     Nov. 14, 2013

(51) Int. Cl.
    *A61K 31/282*     (2006.01)
    *A61K 31/513*     (2006.01)
    *C07F 15/00*     (2006.01)

(52) U.S. Cl.
    USPC ........................... 556/137; 514/492; 424/649

(58) Field of Classification Search
    CPC ............... A61K 31/282; A61K 15/513; C07F 15/0093; C07F 15/0006
    USPC ............................. 514/492; 424/649; 556/137
    See application file for complete search history.

(56) References Cited

U.S. PATENT DOCUMENTS

| | | |
|---|---|---|
| 4,843,161 A | 6/1989 | Lippard et al. |
| 5,244,919 A | 9/1993 | Abrams et al. |

(Continued)

FOREIGN PATENT DOCUMENTS

| | | |
|---|---|---|
| DE | 19623746 A1 | 12/1997 |
| EP | 0 199 524 B1 | 2/1992 |

(Continued)

OTHER PUBLICATIONS

Pascali et al. Eur. J. Inorg. Chem. 2005, 788-796.*

(Continued)

*Primary Examiner* — Savitha Rao
*Assistant Examiner* — Angela Brown-Pettigrew
(74) *Attorney, Agent, or Firm* — Wolf, Greenfield & Sacks, P.C.

(57) ABSTRACT

The present invention is a platinum(II) compound comprising a beta-diketonate ligand represented by the following general formula:

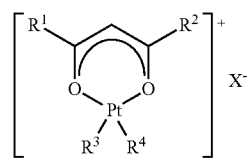

Or general formula:

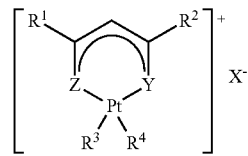

wherein
$R^1$ and $R^2$ are independently selected from the group consisting of alkyl optionally substituted, heteroalkyl optionally substituted, and aryl optionally substituted;
$R^3$ and $R^4$ are independently selected from the group consisting of ammonia, an optionally substituted heterocycle including at least one nitrogen, and an optionally substituted amine, or $R^3$ and $R^4$ can be joined together to form a bidentate ligand
Z and Y are independently selected from the group consisting of O and S, provided at least one of Z and Y is S; and X— is a counterion.
These compounds are useful in the treatment of cancer.

17 Claims, 6 Drawing Sheets

(56) References Cited

U.S. PATENT DOCUMENTS

| | | | |
|---|---|---|---|
| 6,806,289 | B1 | 10/2004 | Lippard et al. |
| 7,138,520 | B2 | 11/2006 | Lippard et al. |
| 2004/0235712 | A1 | 11/2004 | Lippard et al. |
| 2007/0082882 | A1 | 4/2007 | Farrell |
| 2007/0104654 | A1 | 5/2007 | Hsieh et al. |
| 2007/0154398 | A1 | 7/2007 | Wang et al. |
| 2011/0257261 | A1 | 10/2011 | Lippard et al. |
| 2011/0300219 | A1 | 12/2011 | Lippard et al. |
| 2013/0029959 | A1 | 1/2013 | Lippard et al. |

FOREIGN PATENT DOCUMENTS

| | | |
|---|---|---|
| EP | 0 679 656 A1 | 11/1995 |
| WO | WO 2005/092298 A1 | 10/2005 |
| WO | WO 2006/108276 A1 | 10/2006 |
| WO | WO 2007/021852 A2 | 2/2007 |
| WO | WO 2007/124314 A2 | 11/2007 |
| WO | WO 2007/133807 A2 | 11/2007 |
| WO | WO 2008/121949 A1 | 10/2008 |
| WO | WO 2009/032172 A2 | 3/2009 |
| WO | WO 2010/047765 A2 | 4/2010 |
| WO | WO 2010/150036 A1 | 12/2010 |
| WO | WO 2012/177935 A1 | 12/2012 |

OTHER PUBLICATIONS

International Search Report and Written Opinion for PCT/US2008/010213 mailed Mar. 24, 2009.
International Preliminary Report on Patentability for PCT/US2008/010213 mailed Mar. 11, 2010.
International Search Report and Written Opinion for PCT/US2009/004846 mailed Dec. 8, 2009.
International Preliminary Report on Patentability for PCT/US2009/004846 mailed Mar. 10, 2011.
International Search Report and Written Opinion for PCT/US2009/005687 mailed May 26, 2010.
International Preliminary Report on Patentability for PCT/US2009/005687 mailed May 5, 2011.
International Search Report and Written Opinion for PCT/US2012/043620 mailed Sep. 28, 2012.
International Search Report and Written Opinion for PCT/US2012/043626 mailed Oct. 8, 2012.
Al-Allaf et al., Platinum(II) and palladium(II) complexes analogous to oxaliplatin with different cyclohexyldicarboxylate isomeric anions and their in vitro antitumour activity. Structural elucidation of [Pt(C2O4)(cis-dach)]. Transition Metal Chemistry. 2003;28: 717-21.
Ang et al., Transcription inhibition by platinum-DNA cross-links in live mammalian cells. J Am Chem Soc. Jun. 2, 2010;132(21):7429-35. doi: 10.1021/ja101495v.
Bauer et al., Monofunctional platinum amine complexes destabilize DNA significantly. Eur J Biochem. Sep. 1, 1998;256(2):253-60.
Cohen et al., Binding of cis- and trans-dichlorodiammineplatinum(II) to DNA: evidence for unwinding and shortening of the double helix. Science. Mar. 9, 1979;203(4384):1014-6.
Comess et al., Replication inhibition and translesion synthesis on templates containing site-specifically placed cis-diamminedichloroplatinum(II) DNA adducts. Biochemistry. Apr. 28, 1992;31(16):3975-90.
De Pascali et al., Mutagenic Tests Confirm That New Acetylacetonate Pt(II) Complexes Induce Apoptosis in Cancer Cells Interacting with Nongenomic Biological Targets. Met Based Drugs. 2011;2011:763436. doi: 10.1155/2011/763436. Epub Apr. 10, 2011.
Desoize et al., Particular aspects of platinum compounds used at present in cancer treatment. Crit Rev Oncol Hematol. Jun. 2002;42(3):317-25.
Dhar et al., Current Status and Mechanism of Action of Platinum-Based Anticancer Drugs. Bioinorganic Medicinal Chemistry, Enzo Alessio, Ed. Wi-ley-VCH Verlag GmbH & Co. KgaA. Weinheim, Germany, Chapter 3. 2010:79-95.

Dhar et al., Mitaplatin, a potent fusion of cisplatin and the orphan drug dichloroacetate. Proc Natl Acad Sci U S A. Dec. 29, 2009;106(52):22199-204. doi: 10.1073/pnas.0912276106. Epub Dec. 10, 2009.
Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.
Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.
Dhar et al., Targeted single-wall carbon nanotube-mediated Pt(IV) prodrug delivery using folate as a homing device. J Am Chem Soc. Aug. 27, 2008;130(34):11467-76. doi: 10.1021/ja803036e. Epub Jul. 29, 2008.
Feazell et al., Soluble single-walled carbon nanotubes as longboat delivery systems for platinum(IV) anticancer drug design. J Am Chem Soc. Jul. 11, 2007;129(27):8438-9. Epub Jun. 15, 2007.
Fink et al., In vitro and in vivo resistance to cisplatin in cells that have lost DNA mismatch repair. Cancer Res. May 15, 1997;57(10):1841-5.
Fink et al., The role of DNA mismatch repair in platinum drug resistance. Cancer Res. Nov. 1, 1996;56(21):4881-6.
Giandomenico et al., Carboxylation of Kinetically Inert Platinum(IV) Hydroxy Complexes. An Entr.acte.ee into Orally Active Platinum(IV) Antitumor Agents. Inorg Chem. Mar. 1995;34(5):1015-21. doi: 10.1021/ic00109a004.
Gill et al., Synthese, kinetics and mechanism of formation of polynuclear hydroxo-bridged complexes of (trans-1,2-diaminocyclohexane)platinum(II). J Am Chem Soc. 1982;104:4598-604.
Graf et al., Platinum(IV)-chlorotoxin (CTX) conjugates for targeting cancer cells. J Inorg Biochem. May 2012;110:58-63. doi: 10.1016/j.jinorgbio.2012.02.012. Epub Feb. 23, 2012.
Hall et al., Basis for design and development of platinum(IV) anticancer complexes. J Med Chem. Jul. 26, 2007;50(15):3403-11. Epub Jun. 28, 2007.
Hoeschele et al., Synthesis and characterization of diastereomeric (substituted iminodiacetato)(1,2-diaminocyclohexane)platinum(II) complexess. Inorganic Chemistry. 1988;27:4106-13.
Hollis et al., Chemical and biological properties of a new series of cis-diammineplatinum(II) antitumor agents containing three nitrogen donors: cis-[Pt(NH3)2(N-donor)C1]+. J Med Chem. Jan. 1989;32(1):128-36.
Hollis et al., Mechanistic studies of a novel class of trisubstituted platinum(II) antitumor agents. Cancer Res. Apr. 1, 1991;51(7):1866-75.
Hollis et al., Synthesis and Structures of Platinum(III) Complexes of α-Pyridone, [X(NH3)2Pt(C5H4NO)2Pt(NH3)2X](NO3)2*nH2O (X-=C1-, NO2-, Br-). Inorg Chem. 1983;22:3637-44.
Howe-Grant et al., Aqueous Platinum (II) Chemistry; Binding to Biological Molecules. Metal Ions in Biological Systems. Sigel et al., eds. 1980;11:63-125.
Ivanov et al., Biological activity of platinum (II) complexes of the triamine type as a function of their composition and structure. Izv Akad Nauk Ser Biol. May-Jun. 1995;(3):281-90.
Jamieson et al., Structure, Recognition, and Processing of Cisplatin-DNA Adducts. Chem Rev. 1999;99:2467-98.
Jin et al., Platinum(II) triammine antitumour complexes: structure-activity relationship with guanosine 5'-monophosphate (5'-GMP). Inorganica Chimica Acta. 2005;358:677-86.
Jung et al., RNA polymerase II blockage by cisplatin-damaged DNA. Stability and polyubiquitylation of stalled polymerase. J Biol Chem. Jan. 20, 2006;281(3):1361-70. Epub Nov. 7, 2005.
Kapp et al., Dinuclear alkylamine platinum(II) complexes of [1,2-bis(4-fluorophenyl)ethylenediamine]platinum(II): influence of endocytosis and copper and organic cation transport systems on cellular uptake. ChemMedChem. May 2006;1(5):560-4.
Kartalou et al., Mechanisms of resistance to cisplatin. Mutat Res. Jul. 1, 2001;478(1-2):23-43.
Kawai et al., Synthesis, structure and antitumor activity of a new water-soluble platinum complex, (1R,2R-cyclohexanediamine-

(56) References Cited

OTHER PUBLICATIONS

N,N')[2-hydroxy-4-oxo-2-pentenoato(2-)-O2] platinum(II). Chem Pharm Bull (Tokyo). Feb. 1993;41(2):357-61.

Keck et al., Unwinding of supercoiled DNA by platinum-ethidium and related complexes. J Am Chem Soc. 1992;114:3386-90.

Kelland et al., The resurgence of platinum-based cancer chemotherapy. Nat Rev Cancer. Aug. 2007;7(8):573-84. Epub Jul. 12, 2007.

Kidani et al., Antitumor activity of 1,2-diaminocyclohexane—platinum complexes against sarcoma-180 ascites form. J Med Chem. Dec. 1978;21(12):1315-8.

Lebwohl et al., Clinical development of platinum complexes in cancer therapy: an historical perspective and an update. Eur J Cancer. Sep. 1998;34(10):1522-34.

Lee et al., Transcription-coupled and DNA damage-dependent ubiquitination of RNA polymerase II in vitro. Proc Natl Acad Sci U S A. Apr. 2, 2002;99(7):4239-44. Epub Mar. 19, 2002.

Lempers et al., The new antitumor compound, cis-[Pt(NH3)2(4-methylpyridine)Cl]Cl, does not form N7,N7-d(GpG) chelates with DNA. An unexpected preference for platinum binding at the 5'G in d(GpG). J Inorg Biochem. Sep. 1990;40(1):23-35.

Lovejoy et al., cis-Diammine(pyridine)chloroplatinum(II), a monofunctional platinum(II) antitumor agent: Uptake, structure, function, and prospects. Proc Natl Acad Sci U S A. Jul. 1, 2008;105(26):8902-7. doi: 10.1073/pnas.0803441105. Epub Jun. 25, 2008.

Lovejoy et al., Non-traditional platinum compounds for improved accumulation, oral bioavailability, and tumor targeting. Dalton Trans. Dec. 28, 2009;(48):10651-9. doi: 10.1039/b913896j. Epub Oct. 1, 2009.

Lovejoy et al., Spectrum of cellular responses to pyriplatin, a monofunctional cationic antineoplastic platinum(II) compound, in human cancer cells. Mol Cancer Ther. Sep. 2011;10(9):1709-19. doi: 10.1158/1535-7163.MCT-11-0250. Epub Jul. 12, 2011.

Margiotta et al., Sterically hindered complexes of platinum(II) with planar heterocyclic nitrogen donors. A novel complex with 1-methylcytosine has a spectrum of activity different from cisplatin and is able of overcoming acquired cisplatin resistance. J Inorg Biochem. Nov. 2006;100(11):1849-57. Epub Aug. 3, 2006.

Misset et al., Oxaliplatin clinical activity: a review. Crit Rev Oncol Hematol. Aug. 2000;35(2):75-93.

Mukhopadhyay et al., Conjugated platinum(IV)-peptide complexes for targeting angiogenic tumor vasculature. Bioconjug Chem. Jan. 2008;19(1):39-49. Epub Sep. 11, 2007.

Muscella et al., [Pt(O,O'-acac)(gamma-acac)(DMS)], a new Pt compound exerting fast cytotoxicity in MCF-7 breast cancer cells via the mitochondrial apoptotic pathway. Br J Pharmacol. Jan. 2008;153(1):34-49. Epub Nov. 19, 2007.

Muscella et al., New platinum(II) complexes containing both an O,O'-chelated acetylacetonate ligand and a sulfur ligand in the platinum coordination sphere induce apoptosis in HeLa cervical carcinoma cells. Biochem Pharmacol. Jun. 30, 2007;74(1):28-40. Epub Mar. 31, 2007.

Muscella et al., Sublethal concentrations of the platinum(II) complex [Pt(O,O'-acac)(gamma-acac)(DMS)] alter the motility and induce anoikis in MCF-7 cells. Br J Pharmacol. Jul. 2010;160(6):1362-77. doi: 10.1111/j.1476-5381.2010.00782.x.

Page et al., Effect of the diaminocyclohexane carrier ligand on platinum adduct formation, repair, and lethality. Biochemistry. Jan. 30, 1990;29(4):1016-24.

Park et al., Phenanthriplatin, a monofunctional DNA-binding platinum anticancer drug candidate with unusual potency and cellular activity profile. Proc Natl Acad Sci U S A. Jul. 24, 2012;109(30):11987-92. doi: 10.1073/pnas.1207670109. Epub Jul. 6, 2012.

Peer et al., Nanocarriers as an emerging platform for cancer therapy. Nat Nanotechnol. Dec. 2007;2(12):751-60. doi: 10.1038/nnano.2007.387.

Pérez et al., Current status of the development of trans-platinum antitumor drugs. Crit Rev Oncol Hematol. Aug. 2000;35(2):109-20.

Pinto et al., Binding of the antitumor drug cis-diamminedichloroplatinum(II) (cisplatin) to DNA. Biochim Biophys Acta. 1985;780(3):167-80.

Portney et al., Nano-oncology: drug delivery, imaging, and sensing. Anal Bioanal Chem. Feb. 2006;384(3):620-30. Epub Jan. 27, 2006.

Reardon et al., Efficient nucleotide excision repair of cisplatin, oxaliplatin, and Bis-aceto-ammine-dichloro-cyclohexylamine-platinum(IV) (JM216) platinum intrastrand DNA diadducts. Cancer Res. Aug. 15, 1999;59(16):3968-71.

Reardon et al., Purification and characterization of *Escherichia coli* and human nucleotide excision repair enzyme systems. Methods Enzymol. 2006;408:189-213.

Sakai et al., A New One-Dimensional Platinum System Consisting of Carboxylate-Bridged cis-Diammineplatinum Dimers1. JACS. 1998;120:11353-63.

Schwartz et al., Preparation and antitumor evaluation of water-soluble derivatives of dichloro(1,2-diaminocyclohexane)platinum(II). Cancer Treat Rep. Nov. 1977;61(8):1519-25.

Silverman et al., 2.4-A crystal structure of the asymmetric platinum complex [Pt(ammine)(cyclohexylamine)]2+ bound to a dodecamer DNA duplex. J Biol Chem. Dec. 20, 2002;277(51):49743-9. Epub Oct. 10, 2002.

Spingler et al., 2.4 A crystal structure of an oxaliplatin 1,2-d(GpG) intrastrand cross-link in a DNA dodecamer duplex. Inorg Chem. Oct. 22, 2001;40(22):5596-602.

Stephen et al., The structural characterisation and elucidation of the electronic structure of the mononuclear Pt(III) complex [Pt([9]aneS3)2]3+ ([9]aneS3=1,4,7-trithiacyclononane). Chem Commun (Camb). Nov. 30, 2008;(44):5707-9. doi: 10.1039/b811645h. Epub Sep. 30, 2008.

Takahara et al., Crystal structure of the anticancer drug cisplatin bound to duplex DNA. J Am Chem Soc. 1996;118:12309-21.

Todd et al., Inhibition of transcription by platinum antitumor compounds. Metallomics. 2009;1(4):280-91. doi: 10.1039/b907567d.

Trafton, MIT researchers see alternative to common colorectal cancer drug. News Office. Jun. 17, 2008. Last accessed Jun. 23, 2008. 2 pages.

Wang et al., Cellular processing of platinum anticancer drugs. Nat Rev Drug Discov. Apr. 2005;4(4):307-20.

Wang et al., X-ray structure and mechanism of RNA polymerase II stalled at an antineoplastic monofunctional platinum-DNA adduct. Proc Natl Acad Sci U S A. May 25, 2010;107(21):9584-9. doi: 10.1073/pnas.1002565107. Epub May 6, 2010.

Weiss et al., New cisplatin analogues in development. A review. Drugs. Sep. 1993;46(3):360-77.

Whittaker et al., The interaction of DNA-targeted platinum phenanthridinium complexes with DNA. Nucleic Acids Res. Sep. 1, 1998;26(17):3933-9.

Wilson et al., Acetate-bridged platinum(III) complexes derived from cisplatin. Inorg Chem. Sep. 17, 2012;51(18):9852-64. doi: 10.1021/ic301289j. Epub Sep. 4, 2012.

Wilson et al., In vitro anticancer activity of cis-diammineplatinum(II) complexes with β-diketonate leaving group ligands. J Med Chem. Jun. 14, 2012;55(11):5326-36. doi: 10.1021/jm3002857. Epub May 18, 2012.

Wilson et al., Synthesis, characterization, and cytotoxicity of platinum(IV) carbamate complexes. Inorg Chem. Apr. 4, 2011;50(7):3103-15. doi: 10.1021/ic2000816. Epub Mar. 1, 2011.

Wilson, New Constructs for Platinum Anticancer Prodrugs. Presentation. Oct. 19, 2011. 41 pages.

Wong et al., Current status of platinum-based antitumor drugs. Chem Rev. Sep. 8, 1999;99(9):2451-66.

Yalçin, Studies on cis-DDP, [Pt(Dach)(MePhSO)Cl]+ and [PtNH3)2(N-Py)Cl]+ binding to fumarase. Drug Metabol Drug Interact. 1995;12(2):105-15.

Yonezawa et al., Cisplatin and oxaliplatin, but not carboplatin and nedaplatin, are substrates for human organic cation transporters (SLC22A1-3 and multidrug and toxin extrusion family). J Pharmacol Exp Ther. Nov. 2006;319(2):879-86. Epub Aug. 16, 2006.

(56) References Cited

OTHER PUBLICATIONS

Zamble et al., Cisplatin and DNA repair in cancer chemotherapy. Trends Biochem Sci. Oct. 1995;20(10):435-9.

Zamble et al., Repair of cisplatin—DNA adducts by the mammalian excision nuclease. Biochemistry. Aug. 6, 1996;35(31):10004-13.

Zhang et al., Organic cation transporters are determinants of oxaliplatin cytotoxicity. Cancer Res. Sep. 1, 2006;66(17):8847-57.

Zhu et al., Monofunctional platinum-DNA adducts are strong inhibitors of transcription and substrates for nucleotide excision repair in live mammalian cells. Cancer Res. Feb. 1, 2012;72(3):790-800. doi: 10.1158/0008-5472.CAN-11-3151. Epub Dec. 16, 2011.

* cited by examiner

PLATINUM COMPOUNDS AS TREATMENT FOR CANCERS, AND RELATED METHODS, KITS, AND COMPOSITIONS

STATEMENT REGARDING FEDERALLY SPONSORED RESEARCH OR DEVELOPMENT

This invention was made with government support under Grant No. R01 CA034992 awarded by the National Institutes of Health. The government has certain rights in this invention.

FIELD OF THE INVENTION

The present invention relates to compositions, kits, and methods for treatment of cancers. In some embodiments, the compositions, kits, and methods comprise a platinum (e.g., Pt(II) or Pt(IV)) compound comprising a beta-diketonate ligand.

BACKGROUND OF THE INVENTION

Cisplatin is an effective anticancer drug that is used clinically worldwide. Toxic side effects associated with the clinical use of this drug were the impetus for the development of the second-generation platinum chemotherapeutic agent, carboplatin These two drugs operate by the same mechanism. The labile ligands of the coordination complexes, chloride for cisplatin and 1,1-cyclobutanedicarboxylate (CBDCA) for carboplatin, are displaced by water or other biological nucleophiles, and the reactive cis-diammineplatinum(II) moiety binds to nuclear DNA. The resulting platinum-DNA adducts ultimately lead to cell death through transcription inhibition and the ensuing downstream effects. Since cisplatin and carboplatin bear the same $NH_3$ non-leaving group ligands, the nature of the resulting DNA adducts are the same, and therefore the drugs exhibit the same spectrum of activity. Carboplatin, however, is significantly less toxic than cisplatin. The typical patient dose for carboplatin is approximately ten times greater than that of cisplatin (400 mg/m$^2$ versus 40 mg/m$^2$), and the dose-limiting toxic side effect of carboplatin is myelosuppression in contrast to nephrotoxicity, which is dose-limiting for cisplatin treatment. These important clinical differences between cisplatin and carboplatin indicate that the leaving group ligands play an integral role in modulating toxic side effects. Modifications of the leaving group ligands may lead to new platinum anticancer drug candidates.

Accordingly, improved compositions and methods are needed.

SUMMARY OF THE INVENTION

In some embodiments, a compound is provided having the structure:

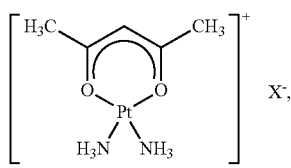

-continued

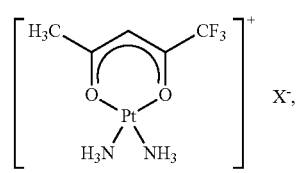

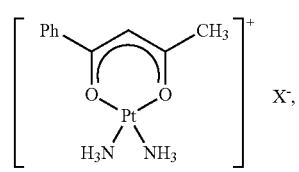

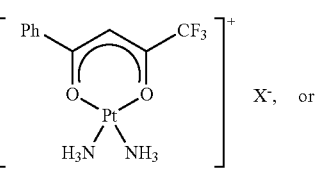

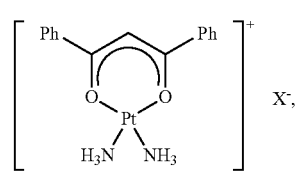

wherein $X^-$ is a counterion.

In some embodiments, a compound is provided having the structure:

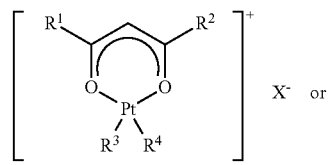

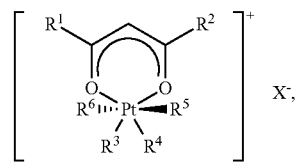

wherein:

$R^1$ and $R^2$ are independently selected from the group consisting of alkyl optionally substituted, heteroalkyl optionally substituted, and aryl optionally substituted, provided at least one of $R^1$ or $R^2$ is not alkyl or haloalkyl;

$R^3$ and $R^4$ are independently selected from the group consisting of ammonia, an optionally substituted heterocycle including at least one nitrogen, and an optionally substituted amine, or $R^3$ and $R^4$ can be joined together to form a bidentate ligand;

$R^5$ and $R^6$ are independently selected from the group consisting of hydroxyl, alkoxy, aryloxy, and acyloxy, each optionally substituted; and $X^-$ is a counterion.

In some embodiments, a compound is provided having the structure:

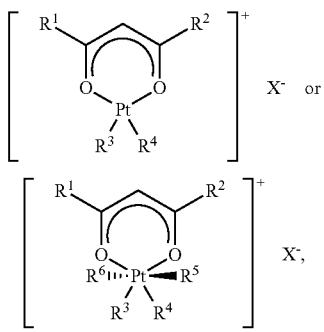

wherein:

R$^1$ and R$^2$ are independently selected from the group consisting of alkyl optionally substituted, heteroalkyl optionally substituted, and aryl optionally substituted, provided at least one of R$^1$ or R$^2$ is aryl optionally substituted;

R$^3$ and R$^4$ are independently selected from the group consisting of ammonia, an optionally substituted heterocycle including at least one nitrogen, and an optionally substituted amine, or R$^3$ and R$^4$ can be joined together to form a bidentate ligand;

R$^5$ and R$^6$ are independently selected from the group consisting of hydroxyl, alkoxy, aryloxy, and acyloxy, each optionally substituted; and X$^-$ is a counterion.

In some embodiments, a compound is provided having the structure:

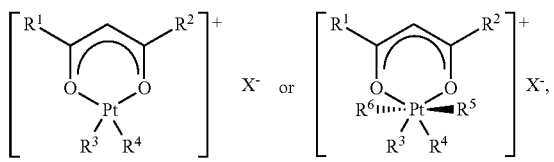

wherein:

R$^1$ and R$^2$ are independently selected from the group consisting of alkyl optionally substituted, heteroalkyl optionally substituted, and aryl optionally substituted; and R$^3$ and R$^4$ are independently selected from the group consisting of ammonia an optionally substituted heterocycle including at least one nitrogen, and an optionally substituted amine;

R$^5$ and R$^6$ are independently selected from the group consisting of hydroxyl, alkoxy, aryloxy, and acyloxy, each optionally substituted; and X$^-$ is a counterion.

In some embodiments, a compound is provided having the structure:

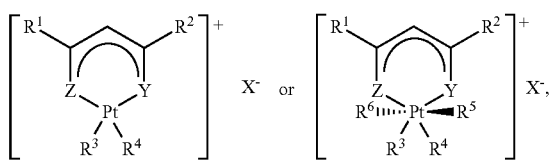

wherein:

R$^1$ and R$^2$ are independently selected from the group consisting of alkyl optionally substituted, heteroalkyl optionally substituted, and aryl optionally substituted;

R$^3$ and R$^4$ are independently selected from the group consisting of ammonia, an optionally substituted heterocycle including at least one nitrogen, and an optionally substituted amine, or R$^3$ and R$^4$ can be joined together to form a bidentate ligand;

R$^5$ and R$^6$ are independently selected from the group consisting of hydroxyl, alkoxy, aryloxy, and acyloxy, each optionally substituted;

Z and Y are independently selected from the group consisting of O and S, provided at least one of Z and Y is S; and X$^-$ is a counterion.

In some embodiments, a method for treating a subject having a cancer are provided comprising administering a therapeutically-effective amount of a compound described herein to a subject having a cancer.

In some embodiments, a method is provided comprising promoting the inhibition or treatment of a cancer in a subject susceptible to or exhibiting symptoms of a cancer via administration to the patient of a composition comprising a compound as described herein.

In some embodiments, a kit for treatment of a cancer is provided comprising a composition comprising a compound as described herein and instructions for use of the composition for treatment of a cancer.

In some embodiments, a pharmaceutical composition is provided comprising a compound as described herein and one or more pharmaceutically acceptable carriers, additives, and/or diluents.

In some embodiments, a composition for treating a subject having a cancer is provided, wherein the composition comprises a compound as described herein.

Figure 1:
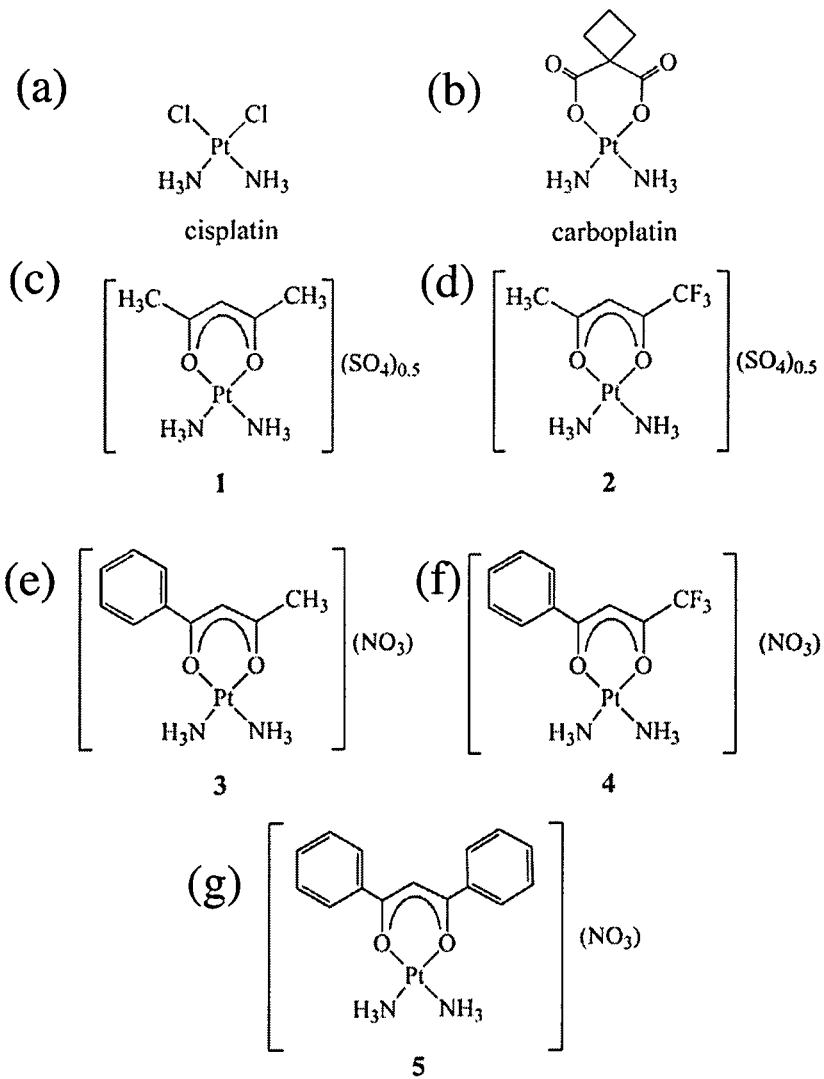
FIGS. 1a-1b show the structures of cisplatin and carboplatin, respectively.
FIGS. 1c-1g show non-limiting examples of compounds of the present invention, according to some embodiments.

Other aspects, embodiments, and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The invention provides compositions, preparations, formulations, kits, and methods useful for treating subjects having cancer or at risk of developing cancer. In some embodiments, the compositions, preparations, formulations, kits, and methods comprise a platinum (e.g., Pt(II) or Pt(IV)) compound comprising a beta-diketonate ligand.

In some aspects, the invention provides compounds and related compositions for use in treating subjects known to have (e.g., diagnosed with) cancer or subjects at risk of developing cancer. In some embodiments, methods of the invention include administering to a subject a therapeutically effective amount of a compound, or a therapeutic preparation, composition, or formulation of the compound as described herein, to a subject having a cancer, who is otherwise free of indications for treatment with said compound. In a particular embodiment, the subject is a human.

In some embodiments, platinum compound (e.g., Pt(II) or Pt(IV) comprising a beta-diketonate ligand are provided. In some embodiments, a compound is provided having the structure:

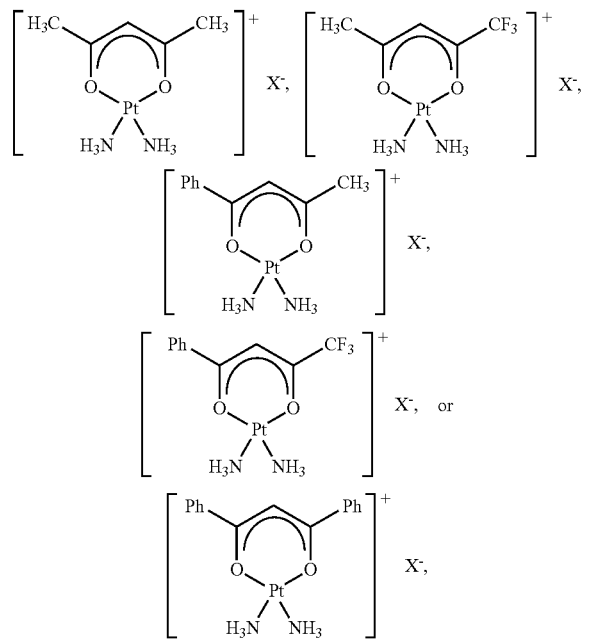

wherein X⁻ is a counterion. In some embodiments, a compound is provided having the structure as shown in any one of FIGS. 1c-1g. In some embodiments, a compound is provided having the structure:

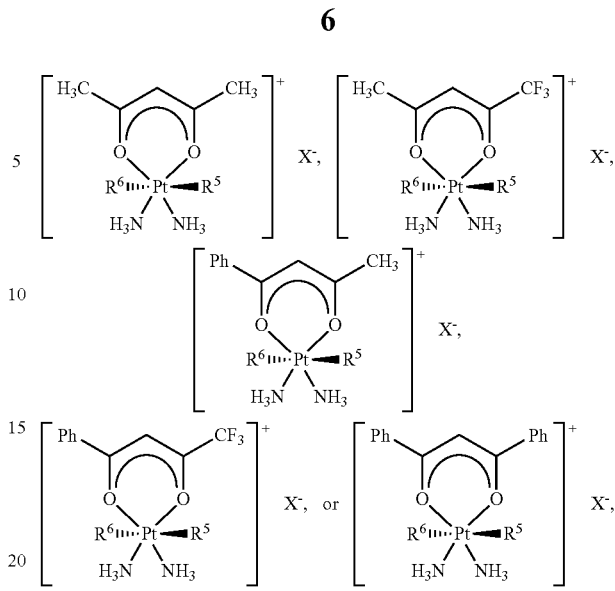

wherein:
R⁵ and R⁶ are independently selected from the group consisting of hydroxyl, alkoxy, aryloxy, and acyloxy, each optionally substituted; and
X⁻ is a counterion.

In some embodiments, a compound is provided having the structure:

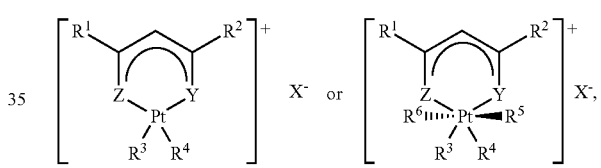

wherein:
R¹ and R² are independently selected from the group consisting of alkyl optionally substituted, heteroalkyl optionally substituted, and aryl optionally substituted;
R³ and R⁴ are independently selected from the group consisting of ammonia, an optionally substituted heterocycle including at least one nitrogen, and an optionally substituted amine, or R³ and R⁴ can be joined together to form a bidentate ligand;
R⁵ and R⁶ are independently selected from the group consisting of hydroxyl, alkoxy, aryloxy, and acyloxy, each optionally substituted;
Z and Y are independently selected from the group consisting of O and S, provided at least one of Z and Y is S; and
X⁻ is a counterion. In some embodiments, Z is O and Y is S. In some embodiments Z is S and Y is O. In some embodiments, each of Z and Y is S.

In some embodiments, a compound is provided having the structure:

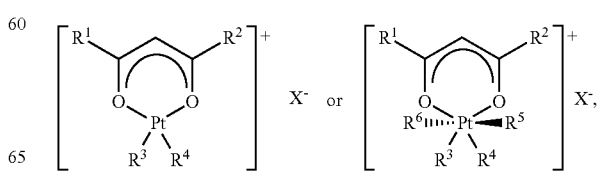

wherein:

$R^1$ and $R^2$ are independently selected from the group consisting of alkyl optionally substituted, heteroalkyl optionally substituted, and aryl optionally substituted, provided at least one of $R^1$ or $R^2$ is not alkyl or haloalkyl;

$R^3$ and $R^4$ are independently selected from the group consisting of ammonia, an optionally substituted heterocycle including at least one nitrogen, and an optionally substituted amine, or $R^3$ and $R^4$ can be joined together to form a bidentate ligand;

$R^5$ and $R^6$ are independently selected from the group consisting of hydroxyl, alkoxy, aryloxy, and acyloxy, each optionally substituted; and $X^-$ is a counterion.

In some embodiments, at least one of $R^1$ or $R^2$ is not alkyl or haloalkyl. In some embodiments, at least one of $R^1$ or $R^2$ is not unsubstituted alkyl or haloalkyl. In some embodiments, at least one of $R^1$ or $R^2$ is not $—CH_3$. In some embodiments, at least one of $R^1$ or $R^2$ is not $—CF_3$. In some embodiments, at least one of $R^1$ or $R^2$ is not $—CF_3$ or $—CH_3$. In some embodiments, one of $R^1$ or $R^2$ is alkyl or haloalkyl and the other of $R^1$ or $R^2$ is not alkyl or haloalkyl. In some embodiments, one of $R^1$ or $R^2$ is unsubstituted alkyl or haloalkyl and the other of $R^1$ or $R^2$ is not unsubstituted alkyl or haloalkyl. In some embodiments, one of $R^1$ or $R^2$ is $—CF_3$ and the other of $R^1$ or $R^2$ is not alkyl or haloalkyl. In some embodiments, one of $R^1$ or $R^2$ is $—CF_3$ and the other of $R^1$ or $R^2$ is not unsubstituted alkyl or haloalkyl. In some embodiments, one of $R^1$ or $R^2$ is $—CH_3$ and the other of $R^1$ or $R^2$ is not alkyl or haloalkyl. In some embodiments, one of $R^1$ or $R^2$ is $—CH_3$ and the other of $R^1$ or $R^2$ is not unsubstituted alkyl or haloalkyl. In some embodiments, one of $R^1$ or $R^2$ is $—CH_3$ or $—CF_3$ and the other of $R^1$ or $R^2$ is not $—CH_3$ or $—CF_3$.

In some embodiments, a compound is provided having the structure:

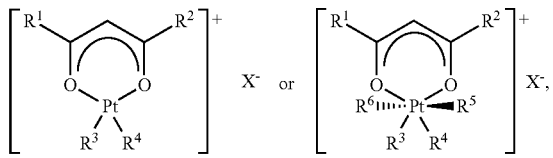

wherein:

$R^1$ and $R^2$ are independently selected from the group consisting of alkyl optionally substituted, heteroalkyl optionally substituted, and aryl optionally substituted, provided at least one of $R^1$ or $R^2$ is aryl optionally substituted;

$R^3$ and $R^4$ are independently selected from the group consisting of ammonia, an optionally substituted heterocycle including at least one nitrogen, and an optionally substituted amine, or $R^3$ and $R^4$ can be joined together to form a bidentate ligand;

$R^5$ and $R^6$ are independently selected from the group consisting of hydroxyl, alkoxy, aryloxy, and acyloxy, each optionally substituted; and $X^-$ is a counterion.

In some embodiments, at least one of $R^1$ or $R^2$ is aryl optionally substituted. In some embodiments, at least one of $R^1$ or $R^2$ is phenyl optionally substituted. In some embodiments, at least one of $R^1$ or $R^2$ is unsubstituted phenyl. In some embodiments, one of $R^1$ or $R^2$ is alkyl or haloalkyl and the other of $R^1$ or $R^2$ is aryl optionally substituted. In some embodiments, one of $R^1$ or $R^2$ is alkyl or haloalkyl and the other of $R^1$ or $R^2$ is phenyl optionally substituted. In some embodiments, one of $R^1$ or $R^2$ is alkyl or haloalkyl and the other of $R^1$ or $R^2$ is unsubstituted phenyl. In some embodiments, one of $R^1$ or $R^2$ is unsubstituted alkyl or haloalkyl and the other of $R^1$ or $R^2$ is aryl optionally substituted. In some embodiments, one of $R^1$ or $R^2$ is unsubstituted alkyl or haloalkyl and the other of $R^1$ or $R^2$ is phenyl optionally substituted. In some embodiments, one of $R^1$ or $R^2$ is unsubstituted alkyl or haloalkyl and the other of $R^1$ or $R^2$ is unsubstituted phenyl. In some embodiments, one of $R^1$ or $R^2$ is $—CF_3$ or $—CH_3$ and the other of $R^1$ or $R^2$ is aryl optionally substituted. In some embodiments, one of $R^1$ or $R^2$ is $—CF_3$ or $—CH_3$ and the other of $R^1$ or $R^2$ is phenyl optionally substituted. In some embodiments, one of $R^1$ or $R^2$ is $—CF_3$ or $—CH_3$ and the other of $R^1$ or $R^2$ is unsubstituted phenyl.

In some embodiments, a compound is provided having the structure:

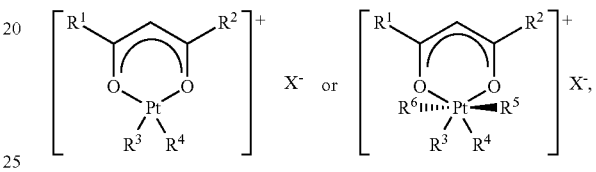

wherein:

$R^1$ and $R^2$ are independently selected from the group consisting of alkyl optionally substituted, heteroalkyl optionally substituted, and aryl optionally substituted; and $R^3$ and $R^4$ are independently selected from the group consisting of ammonia, an optionally substituted heterocycle including at least one nitrogen and an optionally substituted amine;

$R^5$ and $R^6$ are independently selected from the group consisting of hydroxyl, alkoxy, aryloxy, and acyloxy, each optionally substituted; and $X^-$ is a counterion.

In some embodiments, at least one of $R^3$ and $R^4$ is $NH_3$. In some embodiments, each of $R^3$ and $R^4$ is $NH_3$. In some embodiments, at least one of $R^1$ and $R^2$ is phenyl, optionally substituted. In some embodiments, at least one of $R^1$ and $R^2$ is unsubstituted phenyl. In some embodiments, at least one of $R^1$ is $—CH_3$ and $R^2$ is aryl, optionally substituted. In some embodiments, at least one of $R^1$ is $—CH_3$ and $R^2$ is phenyl, optionally substituted. In some embodiments, at least one of $R^1$ is $—CH_3$ and $R^2$ is unsubstituted phenyl. In some embodiments, at least one of $R^1$ is $—CF_3$ and $R^2$ is aryl, optionally substituted. In some embodiments, at least one of $R^1$ is $—CF_3$ and $R^2$ is phenyl, optionally substituted. In some embodiments, at least one of $R^1$ is $—CF_3$ and $R^2$ is unsubstituted phenyl. In some embodiments, each of $R^1$ and $R^2$ is aryl, optionally substituted. In some embodiments, each of $R^1$ and $R^2$ is phenyl, optionally substituted. In some embodiments, each of $R^1$ and $R^2$ is unsubstituted phenyl. In some embodiments, X is halide, sulphate, or nitrate.

In any of the above structures, in some embodiments, at least one of $R^1$ or $R^2$ is not alkyl or haloalkyl. In some embodiments, at least one of $R^1$ or $R^2$ is not unsubstituted alkyl or haloalkyl. In some embodiments, at least one of $R^1$ or $R^2$ is not $—CH_3$. In some embodiments, at least one of $R^1$ or $R^2$ is not $—CF_3$. In some embodiments, at least one of $R^1$ or $R^2$ is not $—CF_3$ or $—CH_3$. In some embodiments, one of $R^1$ or $R^2$ is alkyl or haloalkyl and the other of $R^1$ or $R^2$ is not alkyl or haloalkyl. In some embodiments, one of $R^1$ or $R^2$ is unsubstituted alkyl or haloalkyl and the other of $R^1$ or $R^2$ is not unsubstituted alkyl or haloalkyl. In some embodiments, one of $R^1$ or $R^2$ is —$CF_3$ and the other of $R^1$ or $R^2$ is not alkyl or haloalkyl. In some embodiments, one of $R^1$ or $R^2$ is —$CF_3$ and the other of $R^1$ or $R^2$ is not unsubstituted alkyl or haloalkyl. In some embodiments, one of $R^1$ or $R^2$ is —$CH_3$ and the other of $R^1$ or $R^2$ is not alkyl or haloalkyl. In some embodiments, one of $R^1$ or $R^2$ is —$CH_3$ and the other of $R^1$ or $R^2$ is not unsubstituted alkyl or haloalkyl. In some embodiments, one of $R^1$ or $R^2$ is —$CH_3$ or —$CF_3$ and the other of $R^1$ or $R^2$ is not —$CH_3$ or —$CF_3$. In some embodiments, one of $R^1$ is —$CH_3$ and the other of $R^1$ or $R^2$ is —$CF_3$.

In any of the above structures, in some embodiments, at least one of $R^1$ or $R^2$ is aryl optionally substituted. In some embodiments, at least one of $R^1$ or $R^2$ is phenyl optionally substituted. In some embodiments, at least one of $R^1$ or $R^2$ is unsubstituted phenyl. In some embodiments, each of $R^1$ and $R^2$ is aryl, optionally substituted. In some embodiments, each of $R^1$ and $R^2$ is phenyl, optionally substituted. In some embodiments, each of $R^1$ and $R^2$ is unsubstituted phenyl.

In any of the above structures, in some embodiments, one of $R^1$ or $R^2$ is alkyl or haloalkyl and the other of $R^1$ or $R^2$ is aryl optionally substituted. In some embodiments, one of $R^1$ or $R^2$ is alkyl or haloalkyl and the other of $R^1$ or $R^2$ is phenyl optionally substituted. In some embodiments, one of $R^1$ or $R^2$ is alkyl or haloalkyl and the other of $R^1$ or $R^2$ is unsubstituted phenyl. In some embodiments, one of $R^1$ or $R^2$ is unsubstituted alkyl or haloalkyl and the other of $R^1$ or $R^2$ is aryl optionally substituted. In some embodiments, one of $R^1$ or $R^2$ is unsubstituted alkyl or haloalkyl and the other of $R^1$ or $R^2$ is phenyl optionally substituted. In some embodiments, one of $R^1$ or $R^2$ is unsubstituted alkyl or haloalkyl and the other of $R^1$ or $R^2$ is unsubstituted phenyl. In some embodiments, one of $R^1$ or $R^2$ is —$CF_3$ or —$CH_3$ and the other of $R^1$ or $R^2$ is aryl optionally substituted. In some embodiments, one of $R^1$ or $R^2$ is —$CF_3$ or —$CH_3$ and the other of $R^1$ or $R^2$ is phenyl optionally substituted. In some embodiments, one of $R^1$ or $R^2$ is —$CF_3$ or —$CH_3$ and the other of $R^1$ or $R^2$ is unsubstituted phenyl.

In any of the above structures, in some embodiments, $R^3$ and $R^4$ are independently selected from the group consisting of ammonia, an optionally substituted heterocycle comprising at least one nitrogen, and an optionally substituted amine. In some embodiments, at least one or each of $R^3$ and $R^4$ is an optionally substituted amine comprising the structure $N(R^7)_3$, wherein each $R^7$ is independently selected from the group consisting of H, alkyl optionally substituted, and aryl optionally substituted, or optionally two $R^7$ are joined together to form a ring. Non-limiting example of amine groups include $NH_2Cy$ wherein Cy is cyclohexyl and $NH_2(CH_2Ph)$. In any of the above structures, in some embodiments, at least one of $R^3$ and $R^4$ is $NH_3$. In some embodiments, each of $R^3$ and $R^4$ is $NH_3$.

In any of the above structures, in some embodiments, $R^3$ and $R^4$ are joined together to form a ring so that $R^3$ and $R^4$ form a bidentate ligand. A non-limiting example of bidentate ligand is —$N(R^7)_2(C(R^7)_2)_nC(R^7)$— wherein n is 2, 3, 4, 5, or 6 and $R^7$ is as described herein. In some cases, the bidentate ligand is —$NH_2(CH_2)$—$NH_2$— wherein n is 2, 3, 4, 5, or 6.

In any of the above structures, in some embodiments, $R^3$ and $R^4$ may be an optionally substituted heterocycle groups including at least one nitrogen. In some embodiments, the at least one nitrogen is coordinated to the platinum. Non-limiting examples of heterocycle groups including at least one nitrogen include pyridine, imidazole, pyrazine, pyrimidine, pyridazine, acridine, acridin-9-amine, bipyridine, naphthyridine, quinoline, benzoquinoline, benzoisoquinoline, phenanthridine, phenanthridine-1,9-diamine, benzylamine, or substituted derivatives thereof.

In any of the above structures, in some embodiments, $R^5$ and $R^6$ are independently selected from the group consisting of hydroxyl, alkoxy, aryloxy, and acyloxy, each optionally substituted. Non-limiting examples of suitable $R^5$ and $R^6$ groups include —OH, —OAr (e.g., Ar=phenyl), —Obenzyl, and —OC(=O)$R^8$ wherein $R^8$ is hydrogen, optionally substituted alkyl, or optionally substituted aryl.

In some embodiments, a compound described herein may be provided as a salt comprising a positively charged platinum compound and a counterion (e.g., "X"). The counterion X may be a weak or non-nucleophilic stabilizing ion. X may have a charge of (−1), (−2), (−3), etc. In some cases, X has a charge of (−1). In other cases, X has a charge of (−2). Those of ordinary skill in the art will be aware of suitable stoichiometries for use with the compounds of the present invention. For example, in embodiment where the platinum compound has a charge of (+1) and the counterion has a charge of (−1), the ratio of the platinum compound to the counterion is generally 1:1. As another example, in embodiments where the platinum compound has a charge of (+1) and the counterion has a charge of (−2), the ratio of the platinum compound to the counterion is generally 1:2. In some cases, the counterion is a negatively charged and/or non-coordinating ion. In any of the above compounds, X may be any suitable counterion, including, but not limited to, halide (e.g., chloride, bromide, iodide), nitrate, nitrite, sulfate, sulfite, and triflate.

In any of the above structures, in some embodiments, $R^3$ and $R^4$ do not form the bidentate ligand:

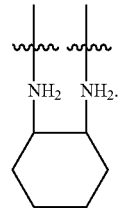

In some embodiments, the compound is not:

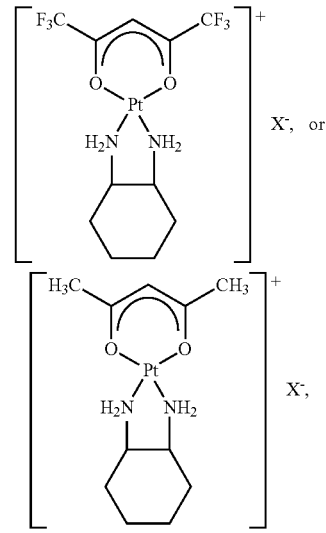

wherein X is a counterion.

In some embodiments, the compound comprises one or more organic or inorganic leaving groups. Additional ligands may coordinate to the metal center, including neutral ligands and/or charged ligands. Neutral ligands include ligands which may coordinate the metal center but do not alter the oxidation state of the metal center. For example, solvent molecules such as water, ammonia, pyridine, and acetonitrile may be neutral ligands. Charged ligands include ligands that may coordinate the metal center and may alter the oxidation state of the metal center. Examples of charged ligands include halides, carboxylates, and the like.

In some embodiments, the ligands associated with the platinum center in the platinum compound may include functional groups capable of interaction with a metal center, e.g., heteroatoms such as nitrogen, oxygen, sulfur, and phosphorus. Non-limiting examples of compounds which the ligands may comprise include amines (primary, secondary, and tertiary), aromatic amines, amino groups, amido groups, nitro groups, nitroso groups, amino alcohols, nitriles, imino groups, isonitriles, cyanates, isocyanates, phosphates, phosphonates, phosphites, (substituted) phosphines, phosphine oxides, phosphorothioates, phosphoramidates, phosphonamidites, hydroxyls, carbonyls (e.g., carboxyl, ester and formyl groups), aldehydes, ketones, ethers, carbamoyl groups, thiols, sulfides, thiocarbonyls (e.g., thiolcarboxyl, thiolester and thiolformyl groups), thioethers, mercaptans, sulfonic acids, sulfoxides, sulfates, sulfonates, sulfones, sulfonamides, sulfamoyls, and sulfinyls. In other cases, at least some of the ligands may be aryl group, alkenyl group, alkynyl group, or other moiety that may bind the metal atom in either a sigma- or pi-coordinated fashion.

In some embodiments, compounds of the invention may comprise a bidentate ligand which, when bound to a metal center, forms a metallacycle structure with the metal center. Bidentate ligands suitable for use in the present invention include species having at least two sites capable of binding to a metal center. For example, the bidentate ligand may comprise at least two heteroatoms that coordinate the metal center, or a heteroatom and an anionic carbon atom that coordinate the metal center. Examples of bidentate ligands suitable for use in the invention include, but are not limited to, alkyl and aryl derivatives of moieties such as amines, phosphines, phosphites, phosphates, thiolates, imines, oximes, ethers, hybrids thereof, substituted derivatives thereof, aryl groups (e.g., bis-aryl, heteroaryl-substituted aryl), heteroaryl groups, and the like. Specific examples of bidentate ligands include ethylene diamine, 2,2'-bipyridine, acetylacetonate, mono- and dithioacetylacetonate, oxalate, thiooxalate, and the like.

In some embodiments, compounds of the invention may comprise a tridentate ligand, which includes species which have at least three sites capable of binding to a metal center. For example, the bidentate ligand may comprise at least three heteroatoms that coordinate the metal center, or a combination of heteroatom(s) and anionic carbon atom(s) that coordinate the metal center.

In some embodiments, compounds of the invention comprise one or more leaving groups. As used herein, a "leaving group" is given its ordinary meaning in the art and refers to an atom or a group capable of being displaced by a nucleophile. Examples of suitable leaving groups include, but are not limited to, halides (such as chloride, bromide, and iodide), alkanesulfonyloxy, arenesulfonyloxy, alkyl-carbonyloxy (e.g., acetoxy, carboxylate), arylcarbonyloxy, mesyloxy, tosyloxy, trifluoromethane-sulfonyloxy, aryloxy, methoxy, N,O-dimethylhydroxylamino, pixyl, oxalato, malonato, and the like. A leaving group may also be a bidentate, tridentate, or other multidentate ligand. In some embodiments, the leaving group is a halide or carboxylate. In some embodiments, the leaving group is chloride. In some embodiments, the leaving group is the beta-diketonate.

Some embodiments of the invention comprise compounds having two leaving groups positioned in a cis configuration, i.e., the compound may be a cis isomer. However, it should be understood that compounds of the invention may also have two leaving groups positioned in a trans configuration, i.e., the compound may be a trans isomer. Those of ordinary skill in the art would understand the meaning of these terms.

In some embodiments, the compound has a molecular weight of 1500 g/mol or less, 1500 g/mol or less, 1400 g/mol or less, 1300 g/mol or less, 1200 g/mol or less, 1100 g/mol or less, 1000 g/mol or less, 900 g/mol or less, 800 g/mol or less, 700 g/mol or less (e.g., 700 Da or less).

Pt(II) and Pt(IV) complexes of the invention may be synthesized according to methods known in the art, including various methods described herein. For example, the method may comprise reaction of cisplatin with one or more ligand sources. In some cases, a Pt(IV) complex can be obtained by reaction of the parent Pt(II) species with, for example, hydrogen peroxide at temperatures ranging between 25-60° C. in an appropriate solvent, such as water or N,N-dimethylformamide.

In some embodiments, a method for treating a subject having a cancer is provided comprising administering a therapeutically-effective amount of a compound as described herein to a subject having a cancer. In some embodiments, a method is provided comprising promoting the inhibition or treatment of a cancer in a subject susceptible to or exhibiting symptoms of a cancer via administration to the patient of a composition comprising a compound as described herein. In some embodiments, a kit for treatment of a cancer is provided comprising a composition comprising a compound as described herein and instructions for use of the composition for treatment of a cancer. In some embodiments, a pharmaceutical composition is provided comprising a compound as described herein and one or more pharmaceutically acceptable carriers, additives, and/or diluents. In some embodiments, a composition for treating a subject having a cancer is provided wherein the composition comprises a compound as described herein.

In some embodiments, method for treating a subject having a cancer are provided, wherein the method comprises administering a therapeutically effective amount of a compound, as described herein, to a subject having a cancer or suspected of having cancer. In some cases, the subject may be otherwise free of indications for treatment with said compound. In some cases, methods include use of cancer cells, including but not limited to mammalian cancer cells. In some instances, the mammalian cancer cells are human cancer cells.

In some embodiments, the compounds of the invention have one or more desirable, but unexpected, combinations of properties, including increased activity and/or cytotoxicity, and reduction of adverse side effects. In some embodiments, the compounds described herein are tunable and the substituents can be varied to provide the desirable balance between various properties, including lipophilicity and cell toxicity. In some cases, the variation of the substituents about the beta-diketonate ligand allows for alterations of the hydrophobicity and electron-withdrawing properties of the leaving groups ligands so as to provide different anticancer efficacies in vitro.

In some embodiments, a compound as described herein has a log P value (e.g., lipophilicity) of about 0.1, about 0.2, about 0.3, about 0.4, about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, or about 4.0, or greater, or any range of values there between. In some cases, a compound has a log P value of between about 0 and about 4, between about 1 and about 4, between about 2 and about 4, or between about 1 and about 3, or between about 1.5 and about 2.5, or between about 2 and about 3. In some cases, the log P value is about 2.15. Those of ordinary skill in the art will be aware of suitable methods for determining the log P value of a compound, for example, as described in the Examples section. In some embodiments, the log P value may be determined using the method described in the OECD Guidelines for the Testing of Chemicals, Test No. 107: Partition Coefficient (n-octanol/water): Shake Flask Method, adopted on Jul. 27, 1995. In some embodiments, the log P value may be tuned and/or selected by selection of the appropriate substituents on the beta-diketonate ligand.

In some embodiments, a compound as described herein has an $IC_{50}$ of about or less than about 30 uM (micromolar), about or less than about 28 uM, about or less than about 26 uM, about or less than about 24 uM, about or less than about 22 uM, about or less than about 20 uM, about or less than about 18 uM, about or less than about 16 uM, about or less than about 15 uM, about or less than about 14 uM, about or less than about 13 uM, about or less than about 12 uM, about or less than about 11 uM, about or less than about 10 uM, about or less than about 9 uM, about or less than about 8 uM, about or less than about 7 uM, about or less than about 6 uM, about or less than about 5 uM, about or less than about 4 uM, about or less than about 3 uM, about or less than about 2 uM, about or less than about 1.5 uM, about or less than about 1.0 uM, about or less than about 0.9 uM, about or less than about 0.8 uM, about or less than about 0.7 uM, about or less than about 0.6 uM, about or less than about 0.5 uM, about or less than about 0.4 uM, about or less than about 0.3 uM, about or less than about 0.2 uM, about or less than about 0.1 uM, or less.

In some embodiments, the compounds of the present invention substantially affect cancer cells and have no substantial effect on non-cancerous cells (e.g., the agent is substantially inactive towards non-cancerous cells) by determining the ratio of cancer cells which are affected (e.g., resulting in cell death by the agent) to non-cancerous cells which are affected, following exposure to the therapeutically active agent. For example, the ratio of cancer cells to non-cancerous cells which are affected (e.g., cell death) upon exposure to a therapeutically active agent is at least about 10:1, at least about 100:1, at least about 500:1, at least about 1000:1, at least about 5000:1, at least about 10,000:1, at least about 100,000:1, or greater. Those of ordinary skill in the art would be aware of methods and technologies for determining the ratio of cancerous cells to non-cancerous cells affected by the agent, as well as the number of cells that undergo cell death upon exposure to the agent. Other parameters may also be determined when determining whether an agent affects a cancer cell and/or a non-cancerous cell, for example, tumor size, membrane potential of a cell, or presence or absence of a compound in parts of the cell (e.g., cytochrome c, apoptosis inducing factor, etc.).

In some embodiments, the compounds of the present invention may be used to prevent the growth of a tumor or cancer, and/or to prevent the metastasis of a tumor or cancer. In some embodiments, compositions or compound of the invention may be used to shrink or destroy a cancer. It should be appreciated that compositions or compound of the invention may be used alone or in combination with one or more additional anti-cancer agents or treatments (e.g., chemotherapeutic agents, targeted therapeutic agents, pseudo-targeted therapeutic agents, hormones, radiation, surgery, etc., or any combination of two or more thereof). In some embodiments, a composition or compound of the invention may be administered to a patient who has undergone a treatment involving surgery, radiation, and/or chemotherapy. In certain embodiments, a composition or compound of the invention may be administered chronically to prevent, or reduce the risk of, a cancer recurrence.

The cancers treatable by methods of the present invention preferably occur in mammals. Mammals include, for example, humans and other primates, as well as pet or companion animals, such as dogs and cats, laboratory animals, such as rats, mice and rabbits, and farm animals, such as horses, pigs, sheep, and cattle. In some embodiments, the compounds of the present invention may be used to treat or affect cancers including, but not limited to lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including malignant melanoma, tumor progression of human skin keratinocytes, squamous cell cancer, thyroid cancer, retinoblastoma, neuroblastoma, peritoneal effusion, malignant pleural effusion, mesothelioma, gall bladder cancer, trophoblastic neoplasms, and hemangiopericytoma. In some cases, the cancer is lung, ovarian, cervix, breast, bone, colorectal, and/or prostate cancer.

In some embodiments, the cancer is breast cancer. In some cases, the breast cancer is metastatic breast cancer. In some cases, the breast cancer is metastatic breast cancer that does not express the gene for the estrogen receptor (e.g., MDA-MB-468). In some cases, the breast cancer is triple-negative breast cancer that does not express the genes for the estrogen receptor, the progresterone receptor, or the Human Epidermal Growth Factor Receptor 2 (HER2).

The invention further comprises compositions (including pharmaceutical compositions), preparations, formulations, kits, and the like, comprising any of the compounds as described herein. In some cases, a pharmaceutical composition is provided comprising a compound as described herein, or a pharmaceutically acceptable salt thereof, and one or more pharmaceutically acceptable carriers, additives and/or diluents. In some cases, a kit (e.g., for the treatment of cancer)

comprises a composition (or a pharmaceutical composition) comprising a compound as described herein and instructions for use of the composition (or a pharmaceutical composition) for treatment of cancer. These and other embodiments of the invention may also involve promotion of the treatment of cancer or tumor according to any of the techniques and compositions and combinations of compositions described herein.

In some embodiments, the present invention provides "pharmaceutical compositions" or "pharmaceutically acceptable" compositions, which comprise a therapeutically effective amount of one or more of the compounds described herein, formulated together with one or more pharmaceutically acceptable carriers (additives) and/or diluents. The pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As set out herein, certain embodiments of the present compounds may contain be formed or provided as a salt, and in some cases, as a pharmaceutically acceptable salt. The term "pharmaceutically-acceptable salt" in this respect refers to the relatively non-toxic, inorganic and organic salts of compounds of the present invention. These salts can be prepared in situ in the administration vehicle or the dosage form manufacturing process, or by separately reacting a purified compound of the invention followed by reaction with a suitable reactant (e.g., suitable organic or inorganic acid and/or base), and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al., "Pharmaceutical Salts," J. Pharm. Sci. 1977, 66, 1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

The compound may be orally administered, parenterally administered, subcutaneously administered, and/or intravenously administered. In certain embodiments, a compound or pharmaceutical preparation is administered orally. In other embodiments, the compound or pharmaceutical preparation is administered intravenously. Alternative routes of administration include sublingual, intramuscular, and transdermal administrations.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, from about 5% to about 70%, or from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes, and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams, and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Delivery systems suitable for use with the present invention include time-release, delayed release, sustained release, or controlled release delivery systems, as described herein. Such systems may avoid repeated administrations of the active compounds of the invention in many cases, increasing convenience to the subject and the physician. Many types of release delivery systems are available and known to those of ordinary skill in the art. They include, for example, polymer based systems such as polylactic and/or polyglycolic acid, polyanhydrides, and polycaprolactone; nonpolymer systems that are lipid-based including sterols such as cholesterol, cholesterol esters, and fatty acids or neutral fats such as mono-, di- and triglycerides; hydrogel release systems; silastic systems; peptide based systems; wax coatings; compressed tablets using conventional binders and excipients; or partially fused implants. Specific examples include, but are not limited to, erosional systems in which the composition is contained in a form within a matrix, or diffusional systems in which an active component controls the release rate. The formulation may be as, for example, microspheres, hydrogels, polymeric reservoirs, cholesterol matrices, or polymeric systems. In some embodiments, the system may allow sustained or controlled release of the active compound to occur, for example, through control of the diffusion or erosion/degradation rate of the formulation. In addition, a pump-based hardware delivery system may be used in some embodiment of the invention.

Use of a long-term release implant may be particularly suitable in some cases. "Long-term release," as used herein, means that the implant is constructed and arranged to deliver therapeutic levels of the composition for at least about 30 or about 45 days, for at least about 60 or about 90 days, or even longer in some cases. Long-term release implants are well known to those of ordinary skill in the art, and include some of the release systems described above.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissue.

When the compounds of the present invention are administered as pharmaceuticals, to humans and animals, they can be given per se or as a pharmaceutical composition containing, for example, about 0.1% to about 99.5%, about 0.5% to about 90%, or the like, of active ingredient in combination with a pharmaceutically acceptable carrier.

The administration may be localized (i.e., to a particular region, physiological system, tissue, organ, or cell type) or systemic, depending on the condition to be treated. For example, the composition may be administered through parental injection, implantation, orally, vaginally, rectally, buccally, pulmonary, topically, nasally, transdermally, surgical administration, or any other method of administration where access to the target by the composition is achieved. Examples of parental modalities that can be used with the invention include intravenous, intradermal, subcutaneous, intracavity, intramuscular, intraperitoneal, epidural, or intrathecal. Examples of implantation modalities include any implantable or injectable drug delivery system. Oral administration may be useful for some treatments because of the convenience to the patient as well as the dosing schedule.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

The compositions of the present invention may be given in dosages, generally, at the maximum amount while avoiding or minimizing any potentially detrimental side effects. The compositions can be administered in effective amounts, alone or in a cocktail with other compounds, for example, other compounds that can be used to treat cancer. An effective amount is generally an amount sufficient to inhibit cancer within the subject.

One of skill in the art can determine what an effective amount of the composition is by screening the ability of the composition using any of the assays described herein. The effective amounts will depend, of course, on factors such as the severity of the condition being treated; individual patient parameters including age, physical condition, size, and weight; concurrent treatments; the frequency of treatment; or the mode of administration. These factors are well known to those of ordinary skill in the art and can be addressed with no more than routine experimentation. In some cases, a maximum dose be used, that is, the highest safe dose according to sound medical judgment.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the subject. For example, chronic treatments may involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. The daily dosage may range from 0.001 to 50 mg of compound per kg of body weight, or from 0.01 to about 10 mg of compound per kg of body weight. In some cases, the dose may range from between about 5 and about 50 mg of compound per kg of body weight, between about 10 and about 40 mg of compound per kg of body weight, between about 10 and about 35 mg of compound per kg of body weight, or between about 15 and about 40 mg of compound per kg of body weight. However, lower or higher doses can be used. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it may be administered as a pharmaceutical formulation (composition) as described above.

The present invention also provides any of the above-mentioned compositions useful for treatment of cancer packaged in kits, optionally including instructions for use of the composition for the treatment of cancer. That is, the kit can include a description of use of the composition for participation in any biological or chemical mechanism disclosed herein associated with cancer or tumor. The kits can further include a description of activity of cancer in treating the pathology, as opposed to the symptoms of the cancer. That is, the kit can include a description of use of the compositions as discussed herein. The kit also can include instructions for use of a combination of two or more compositions of the invention. Instructions also may be provided for administering the drug by any suitable technique, such as orally, intravenously, or via another known route of drug delivery. The invention also involves promotion of the treatment of cancer according to any of the techniques and compositions and composition combinations described herein.

The compositions of the invention, in some embodiments, may be promoted for treatment of abnormal cell proliferation, cancers, or tumors, or includes instructions for treatment of accompany cell proliferation, cancers, or tumors, as mentioned above. In another aspect, the invention provides a method involving promoting the prevention or treatment of cancer via administration of any one of the compositions of the present invention, and homologs, analogs, derivatives, enantiomers and functionally equivalent compositions thereof in which the composition is able to treat cancers. As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention in connection with treatment of cell proliferation, cancers or tumors. "Instructions" can define a component of promotion, and typically involve written instructions on or associated with packaging of compositions of the invention. Instructions also can include any oral or electronic instructions provided in any manner. The "kit" typically defines a package including any one or a combination of the compositions of the invention and the instructions, or homologs, analogs, derivatives, enantiomers and functionally equivalent compositions thereof, but can also include the composition of the invention and instructions of any form that are provided in connection with the composition in a manner such that a clinical professional will clearly recognize that the instructions are to be associated with the specific composition.

The kits described herein may also contain one or more containers, which can contain compounds such as the species, signaling entities, biomolecules, and/or particles as described. The kits also may contain instructions for mixing, diluting, and/or administrating the compounds. The kits also can include other containers with one or more solvents, surfactants, preservatives, and/or diluents (e.g., normal saline (0.9% NaCl), or 5% dextrose) as well as containers for mixing, diluting or administering the components to the sample or to the patient in need of such treatment.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kit, in one set of embodiments, may comprise a carrier means being compartmentalized to receive in close confinement one or more container means such as vials, tubes, and the like, each of the container means comprising one of the separate elements to be used in the method. For example, one of the container means may comprise a positive control in the assay. Additionally, the kit may include containers for other components, for example, buffers useful in the assay.

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

As used herein, a "subject" or a "patient" refers to any mammal (e.g., a human), such as a mammal that may be susceptible to tumorigenesis or cancer. Examples include a human, a non-human primate, a cow, a horse, a pig, a sheep, a goat, a dog, a cat, or a rodent such as a mouse, a rat, a hamster, or a guinea pig. Generally, or course, the invention is directed toward use with humans. A subject may be a subject diagnosed with cancer or otherwise known to have cancer. In certain embodiments, a subject may be selected for treatment on the basis of a known cancer in the subject. In some embodiments, a subject may be selected for treatment on the basis of a suspected cancer in the subject. In some embodiments, a cancer may be diagnosed by detecting a mutation associate in a biological sample (e.g., urine, sputum, whole blood, serum, stool, etc., or any combination thereof. Accordingly, a compound or composition of the invention may be administered to a subject based, at least in part, on the fact that a mutation is detected in at least one sample (e.g., biopsy sample or any other biological sample) obtained from the subject. In some embodiments, a cancer may not have been detected or located in the subject, but the presence of a mutation associated with a cancer in at least one biological sample may be sufficient to prescribe or administer one or more compositions of the invention to the subject. In some embodiments, the composition may be administered to prevent the development of a cancer. However, in some embodiments, the presence of an existing cancer may be suspected, but not yet identified, and a composition of the invention may be administered to prevent further growth or development of the cancer.

It should be appreciated that any suitable technique may be used to identify or detect mutation and/or over-expression associated with a cancer. For example, nucleic acid detection techniques (e.g., sequencing, hybridization, etc.) or peptide detection techniques (e.g., sequencing, antibody-based detection, etc.) may be used. In some embodiments, other techniques may be used to detect or infer the presence of a cancer (e.g., histology, etc.).

The presence of a cancer can be detected or inferred by detecting a mutation, over-expression, amplification, or any combination thereof at one or more other loci associated with a signaling pathway of a cancer.

A "sample," as used herein, is any cell, body tissue, or body fluid sample obtained from a subject. Non-limiting examples of body fluids include, for example, lymph, saliva, blood, urine, and the like. Samples of tissue and/or cells for use in the various methods described herein can be obtained through standard methods including, but not limited to, tissue biopsy, including punch biopsy and cell scraping, needle biopsy; or collection of blood or other bodily fluids by aspiration or other suitable methods.

The phrase "therapeutically effective amount" as used herein means that amount of a compound, material, or composition comprising a compound of the present invention which is effective for producing some desired therapeutic effect in a subject at a reasonable benefit/risk ratio applicable to any medical treatment. Accordingly, a therapeutically effective amount prevents, minimizes, or reverses disease progression associated with a cancer. Disease progression can be monitored by clinical observations, laboratory and imaging investigations apparent to a person skilled in the art. A therapeutically effective amount can be an amount that is effective in a single dose or an amount that is effective as part of a multi-dose therapy, for example an amount that is administered in two or more doses or an amount that is administered chronically.

As used herein, the term "alkyl" is given its ordinary meaning in the art and refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some cases, the alkyl group may be a lower alkyl group, i.e., an alkyl group having 1 to 10 carbon atoms (e.g., methyl, ethyl, propyl, butyl, pentyl, hexyl, heptyl, octyl, nonyl, or decyl). In some embodiments, a straight chain or branched chain alkyl may have 30 or fewer carbon atoms in its backbone, and, in some cases, 20 or fewer. In some embodiments, a straight chain or branched chain alkyl may have 12 or fewer carbon atoms in its backbone (e.g., $C_1$-$C_{12}$ for straight chain, $C_3$-$C_{12}$ for branched chain), 6 or fewer, or 4 or fewer. Likewise, cycloalkyls may have from 3-10 carbon atoms in their ring structure, or 5, 6 or 7 carbons in the ring structure. Examples of alkyl groups include, but are not limited to, methyl, ethyl, propyl, isopropyl, cyclopropyl, butyl, isobutyl, t-butyl, cyclobutyl, hexyl, and cyclochexyl.

The term "heteroalkyl" is given its ordinary meaning in the art and refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, poly(ethylene glycol), and alkyl-substituted amino.

The terms "alkenyl" and "alkynyl" refer to unsaturated aliphatic groups analogous in length and possible substitution to the alkyls described above, but that contain at least one double or triple bond respectively.

The terms "heteroalkenyl" and "heteroalkynyl" refer to unsaturated aliphatic groups analogous in length and possible substitution to the heteroalkyls described above, but that contain at least one double or triple bond respectively.

The term "aryl" is given its ordinary meaning in the art and refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. Substituents include, but are not limited to, any of the previously mentioned substitutents, i.e., the substituents recited for aliphatic moieties, or for other moieties as disclosed herein, resulting in the formation of a stable compound. In some cases, an aryl group is a stable mono- or polycyclic unsaturated moiety having preferably 3-14 carbon atoms, each of which may be substituted or unsubstituted. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" is given its ordinary meaning in the art and refers to aryl groups comprising at least one heteroatom as a ring atom. A "heteroaryl" is a stable heterocyclic or polyheterocyclic unsaturated moiety having preferably 3-14 carbon atoms, each of which may be substituted or unsubstituted. Substituents include, but are not limited to, any of the previously mentioned substitutents, i.e., the substituents recited for aliphatic moieties, or for other moieties as disclosed herein, resulting in the formation of a stable compound. In some cases, a heteroaryl is a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein may be attached via an alkyl or heteroalkyl moiety and thus also include -(alkyl)aryl, -(heteroalkyl)aryl, -(heteroalkyl)heteroaryl, and -(heteroalkyl)heteroaryl moieties. Thus, as used herein, the phrases "aryl or heteroaryl moieties" and "aryl, heteroaryl, -(alkyl)aryl, -(heteroalkyl)aryl, -(heteroalkyl)heteroaryl, and -(heteroalkyl)heteroaryl" are interchangeable. Substituents include, but are not limited to, any of the previously mentioned substituents, i.e., the substituents recited for aliphatic moieties, or for other moieties as disclosed herein, resulting in the formation of a stable compound.

It will be appreciated that aryl and heteroaryl groups (including bicyclic aryl groups) can be unsubstituted or substituted, wherein substitution includes replacement of one or more of the hydrogen atoms thereon independently with any one or more of the following moieties including, but not limited to: aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$F; —CHF$_2$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)R$_x$; —S(O)$_2$R$_x$; —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Additionally, it will be appreciated, that any two adjacent groups taken together may represent a 4, 5, 6, or 7-membered substituted or unsubstituted alicyclic or heterocyclic moiety. Additional examples of generally applicable substituents are illustrated by the specific embodiments described herein.

The term "heterocycle" is given its ordinary meaning in the art and refers to refer to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms.

The term "heterocycle" may include heteroaryl groups, saturated heterocycles (e.g., cycloheteroalkyl) groups, or combinations thereof. The heterocycle may be a saturated molecule, or may comprise one or more double bonds. In some cases, the heterocycle is a nitrogen heterocycle, wherein at least one ring comprises at least one nitrogen ring atom. The heterocycles may be fused to other rings to form a polycyclic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom (e.g., nitrogen). In some cases, the heterocycle is pyridine, imidazole, pyrazine, pyrimidine, pyridazine, acridine, acridin-9-amine, bipyridine, naphthyridine, quinoline, benzoquinoline, benzoisoquinoline, phenanthridine, phenanthridine-1,9-diamine, or the like.

The terms "halo" and "halogen" as used herein refer to an atom selected from the group consisting of fluorine, chlorine, bromine, and iodine.

The terms "carboxyl group," "carbonyl group," and "acyl group" are recognized in the art and can include such moieties as can be represented by the general formula:

wherein W is H, OH, O-alkyl, O-alkenyl, or a salt thereof. Where W is O-alkyl, the formula represents an "ester." Where W is OH, the formula represents a "carboxylic acid." The term "carboxylate" refers to an anionic carboxyl group. In general, where the oxygen atom of the above formula is replaced by sulfur, the formula represents a "thiolcarbonyl"

group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "alkoxy" (or "alkyloxy"), or "thioalkyl" as used herein refers to an alkyl group, as previously defined, attached to the parent molecular moiety through an oxygen atom or through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of alkoxy, include but are not limited to, methoxy, ethoxy, propoxy, isopropoxy, n-butoxy, t-butoxy, neopentoxy and n-hexoxy. Examples of thioalkyl include, but are not limited to, methylthio, ethylthio, propylthio, isopropylthio, n-butylthio, and the like.

The term "alkoxy" refers to the group, —O-alkyl.
The term "aryloxy" refers to the group, —O-aryl.
The term "acyloxy" refers to the group, —O-acyl.
The term "aralkyl" or "arylalkyl," as used herein, refers to an alkyl group substituted with an aryl group.

The terms "amine" and "amino" are art-recognized and refer to both unsubstituted and substituted amines, e.g., a moiety that can be represented by the general formula: N(R')(R'')(R''') wherein R', R'', and R''' each independently represent a group permitted by the rules of valence. An example of a substituted amine is benzylamine. Another non-limiting example of an amine is cyclohexylamine. In some cases, two of R', R'', and R'' may be joined together to form a ring.

It will be appreciated that the above groups and/or compounds, as described herein, may be optionally substituted with any number of substituents or functional moieties. That is, any of the above groups may be optionally substituted. As used herein, the term "substituted" is contemplated to include all permissible substituents of organic compounds, "permissible" being in the context of the chemical rules of valence known to those of ordinary skill in the art. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful for the formation of an imaging agent or an imaging agent precursor. The term "stable," as used herein, preferably refers to compounds which have stability sufficient to allow manufacture and which maintain the integrity of the compound for a sufficient period of time to be detected and preferably for a sufficient period of time to be useful for the purposes detailed herein.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, -carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

The following examples are intended to illustrate certain embodiments of the present invention, but do not exemplify the full scope of the invention.

EXAMPLES AND EMBODIMENTS

Five cationic platinum(II) complexes of the general formula, [Pt(NH$_3$)$_2$(β-diketonate)]X were prepared, where X is a non-coordinating anion and β-diketonate=acetylacetonate (acac), 1,1,1,-trifluoroacetylacetonate (tfac), benzoylacetonate (bzac), 4,4,4-trifluorobenzoylacetonate (tfbz), and dibenzoylmethide (dbm) corresponding to complexes 1-5, respectively (see FIGS. 1c-g). The log P values and the stabilities of 1-5 in aqueous solution were evaluated. The phenyl ring substituents of 3-5 increased the lipophilicities of the resulting complexes, whereas the trifluoromethyl groups of 2 and 4 decreased the stabilities of the complexes in aqueous solutions. The cellular uptakes of 1-5 in HeLa cells increased as the lipophilicity of the investigated complex increased. Cancer cell cytotoxicity studies indicated that 1 and 3 were less active as compared to 2, 4, and 5, which exhibited comparable cytotoxicities to cisplatin. The biological activities of 1-5 were modulated by the substituents on the β-diketonate ligands, which affected both the lipophilicity and aqueous stability of the resulting complex.

Abbreviations Used: acac, acetylacetonate; bzac, benzoylacetonate; CBDCA, 1,1-cyclobutanedicarboxylate; cisplatin, cis-diamminedichloroplatinum(II); dbm, dibenzoylmethide; GFAAS, graphite furnace atomic absorption spectroscopy; hfac, hexafluoroacetylacetonate; IC$_{50}$, 50% growth inhibitory concentration; MTT, (3-(4,5-Dimethylthiazol-2-yl)-2,5-diphenyltetrazolium bromide; DMF, N,N-dimethylformamide; PBS, phosphate buffered saline; SRB, sulforhodamine B; tfac, 1,1,1-trifluoroacetylacetonate; tfbz, 4,4,4-trifluorobenzoylacetonate; TMS, tetramethylsilane.

RESULTS

Synthesis and Characterization

Figure 2:
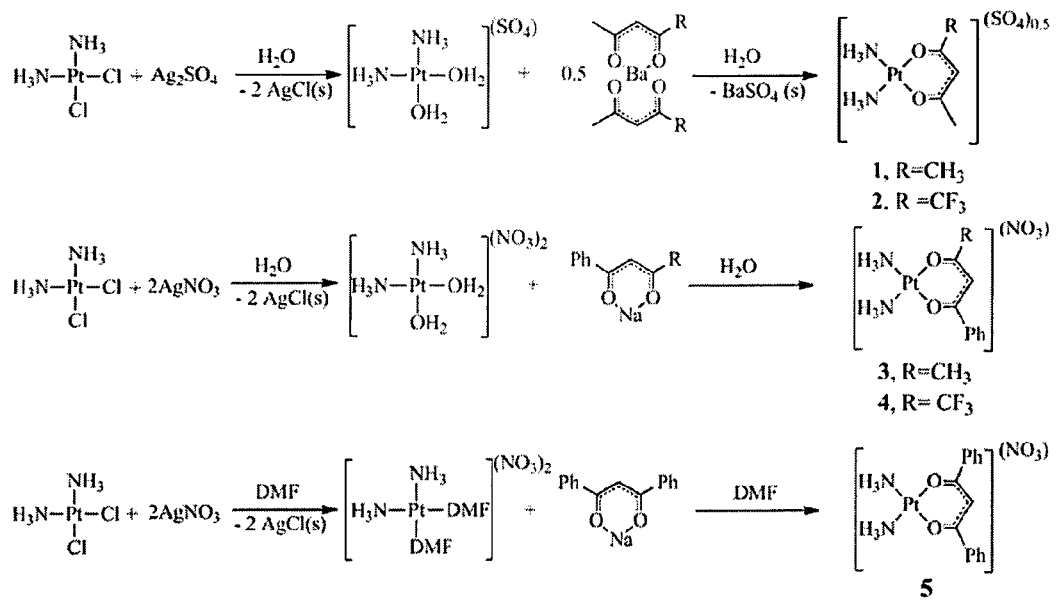
FIG. 2 shows non-limiting examples of synthetic methods for preparing compounds of the present invention, according to some embodiments.

The platinum β-diketonato complexes were synthesized via three different pathways using cisplatin as the common starting material (FIG. 2). In all three routes, cisplatin was first activated by treatment with the desired Ag(I) salt to remove the chloride ligands as insoluble AgCl and generate reactive solvated cis-diammineplatinum(II) cations. Subsequent treatment of the cis-diammineplatinum(II) cations with the appropriate salt of the β-diketonate ligand afforded compounds, 1-5 (FIGS. 1c-g). Different solubilities of the β-diketonate ligands and final platinum(II) complexes resulted in the development of the three slightly modified synthetic routes as shown in FIG. 2 and described in more detail herein.

Characterization of the complexes was achieved by NMR and IR spectroscopy, electrospray ionization mass spectrometry (ESI-MS), and elemental analyses. The presence of nitrate as the counterion for 3-5 was verified both by the characteristic N—O stretching frequency in the IR spectrum near 1383 $cm^{-1}$ and by the m/z peak observed by ESI-MS corresponding to the nitrate adduct, $[2M+NO_3]^+$. In the mass spectra of 1 and 2, only the molecular ion corresponding to the cationic platinum complex was observed. The IR spectra of 1-5 are consistent with O,O' coordination of the acac ligands. Vibrational frequencies between 1560 and 1590 $cm^{-1}$ correspond to C=O stretches, and indicated a decrease in C=O bond order, consistent with π electron delocalization through the six-membered chelate ring. Elemental analyses were consistent with anticipated molecular formulae.

The complexes were also characterized by multinuclear NMR spectroscopy. The low solubility of 2 in aqueous and organic solvent precluded the acquisition of a $^{13}C$ NMR spectrum for this compound. For the other complexes, all expected signals were observed in the $^{13}C$ NMR spectra. The trifluoromethyl groups of 2 and 4 resonate at −76.43 and −76.17 ppm, respectively, in the $^{19}F$ NMR spectra. The $^1H$ NMR spectra display the expected resonances except for the protons of the coordinated $NH_3$ ligands, which are not observed presumably due to rapid exchange with the deuterons of the methanol-$d_4$ NMR solvent. The protons at the gamma position of the β-diketonate ligands resonate between 5.58-6.94 ppm in the five complexes, as summarized in Table 1. The $^{195}Pt$ NMR spectra of the complexes are marked by a single peak that ranges from −1593 to −1454 ppm depending on the β-diketonate ligand (Table 1).

TABLE 1

Selected Multinuclear NMR Chemical Shifts (ppm) for 1-5

| Compound | δ $^1H$, γ position[a] | δ $^{13}C$, γ position[a] | δ $^{195}Pt$[b] | δ $^{19}F$[c] |
|---|---|---|---|---|
| 1 | 5.58 | 103.3 | −1593 | |
| 2 | 6.10 | n.d.[d] | −1497 | −76.43 |
| 3 | 6.32 | 100.3 | −1572 | |
| 4 | 6.72 | 96.5 | −1454 | −76.17 |
| 5 | 6.96 | 97.5 | −1528 | |

Figure 3:
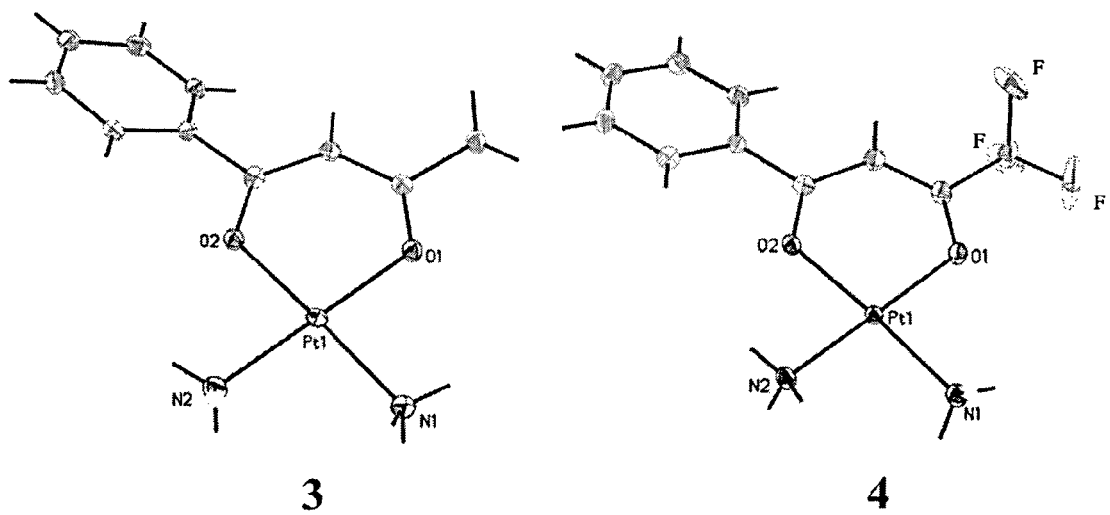
FIG. 3 shows exemplary X-ray crystal structures of some compounds of the present invention, according to some embodiments.

[a]Referenced to $SiMe_4$ at δ = 0 ppm.
[b]Referenced to $Na_2PtCl_6$ at δ = 0 ppm.
[c]Referenced to $CFCl_3$ at δ = 0 ppm.
[d]Not determined Single crystals of 3 and 4 were obtained by vapor diffusion of diethyl ether into methanol solutions, enabling structural determination by X-ray crystallography. The resulting structures are shown in FIG. 3, and relevant bond lengths and angles are collected in Table 2. The structures confirm a square planar coordination geometries of the platinum(II) center and the O,O' coordination mode of the β-diketonate ligands. The nitrate counterions are engaged in hydrogen bonding interactions with the protons of the coordinated $NH_3$ ligands (not shown).

In FIG. 3: X-ray crystal structures of the complex cations of 3 (left) and 4 (right). Ellipsoids are drawn at the 50% probability level.

TABLE 2

Selected Interatomic Distances (Å) and Angles (degrees) for 3 and 4[a]

| | 3 | 4 |
|---|---|---|
| Pt1—N1 | 2.034(2) | 2.017(3) |
| Pt1—N2 | 2.030(2) | 2.015(2) |
| Pt1—O1 | 1.9956(17) | 2.005(2) |
| Pt1—O2 | 1.9907(18) | 1.988(2) |
| O1—Pt1—O2 | 95.20(7) | 94.69(9) |
| O1—Pt1—N1 | 86.81(8) | 88.69(10) |
| O1—Pt1—N2 | 177.62(9) | 176.19(10) |
| O2—Pt1—N1 | 177.79(8) | 176.54(10) |
| O2—Pt1—N2 | 85.37(8) | 86.12(10) |
| N1—Pt1—N2 | 92.65(9) | 90.55(11) |

[a]Atoms are labeled as shown in FIG. 3. Numbers in parentheses are the estimated standard deviations of the last significant figures.

Lipophilicity.

To quantify the lipophilicity of the new platinum complexes, water-octanol partition coefficients (P) were measured using the shake-flask method (e.g., see the OECD Guidelines for the Testing of Chemicals, Test No. 107: Partition Coefficient (n-octanol/water): Shake Flask Method, adopted on Jul. 27, 1995. The resulting log P values are collected in Table 3 and graphically compared in FIG. 4. The measured log P for cisplatin is consistent with literature values. The most lipophilic complex is 5 with a log P value of 0.0±0.1. The overall order of lipophilicity follows the sequence: 5>4>3>2>1. The phenyl groups in 3, 4, and 5 had a larger effect on the lipophilicity than the trifluoromethyl groups of 2 and 4. Substitution of the phenyl group for a methyl group on the β-diketonate ligand led to an increase of lipophilicity by approximately 1 log P unit, whereas the analogous substitution for a trifluoromethyl group led to an increase of approximately 0.3 log P units.

TABLE 3

Experimentally Determined Complex Log P Values and Calculated Ligand Log P Values

| Compound | Complex log P[a] | Calculated Ligand log P[b] |
|---|---|---|
| 1 | −2.67 ± 0.08 | 0.09 ± 0.35 |
| 2 | −2.28 ± 0.07 | 0.72 ± 0.24 |
| 3 | −1.30 ± 0.09 | 1.47 ± 0.43 |
| 4 | −0.98 ± 0.03 | 2.15 ± 0.54 |
| 5 | 0.0 ± 0.1 | 3.08 ± 0.33 |
| cisplatin | −2.21 ± 0.06 | n.d.[c] |

[a]Error are estimated from the standard deviations of repeated experiments.
[b]Errors are the standard deviations obtained from the use of seven different computational algorithms as employed ALOGSP 2.1.
[c]Not determined.

The log P values of the free β-diketonate ligands in the keto form were calculated using the online program ALOGSP 2.1 available at the Virtual Computational Chemistry Laboratory.

Figure 4:
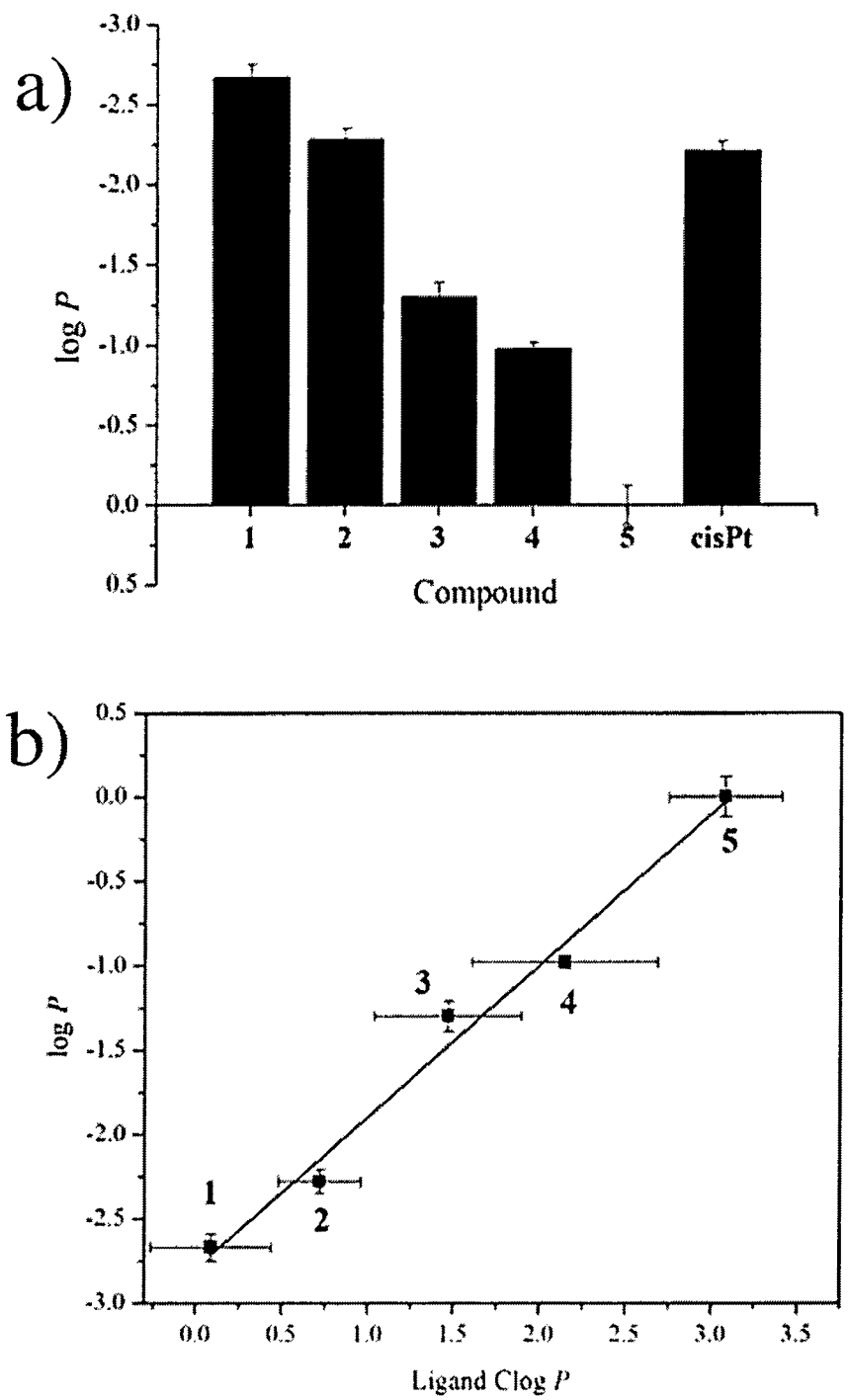
FIG. 4a provides a bar chart representation of experimentally measured log P values of cisplatin and some exemplary compounds of the present invention, according to some embodiments.
FIG. 4b shows a plot of calculated ligand log P values versus experimentally measured complex log P values, according to some embodiments.

These values are displayed in Table 3. The calculated ligand log P values are linearly proportional to the experimentally measured complex log P values (FIG. 4). More lipophilic ligands gave rise to more lipophilic complexes.

In FIG. 4: (a) Bar chart representation of experimentally measured log P values of 1-5 and cisplatin. (b) Plot of calculated ligand log P values versus experimentally measured complex log P values. The line represents the best fit linear regression of the data. The slope and intercept of this line are 0.90±0.06 and −2.8±0.1, respectively. The $R^2$ value is 0.98.

Aquation and Anation Rates.

The stabilities of 1-5 in water and pH 7.4 phosphate buffered saline (PBS) at 37° C. were determined by NMR spectroscopy. The compounds bearing non-fluorinated β-diketonate ligands, 1, 3, and 5, exhibited no changes in the $^1H$ NMR spectra in either medium for up to 25 days. Compounds 2 and 4, which both have a trifluoromethyl group in the ligand backbone, exhibited slow decomposition in water and PBS. In water, the $^1H$ NMR chemical shift of the methyl group of 2 at 2.00 ppm decayed with a half-life of 58 days and concomitant appearance of a new resonance at 2.22 ppm. Over the course of this reaction, the pH changed from 7.5 to 6.3. For 4, the rate of decomposition was quicker. The $^{19}F$ NMR chemical shift at −74.4 ppm of 4 disappeared with a half-life of 29 days, accompanied by the appearance of a new resonance at −76.6 ppm. The pH of this solution remained at 7.5 for the duration of the experiment.

In pH 7.4 PBS, the rates of decomposition increased. The half-lives of 2 and 4 in this medium were 3.4 and 1.8 days, respectively. For 4, the final product was the same as that observed in the aquation in non-buffered water characterized by a $^{19}F$ NMR chemical shift at −76.6 ppm. Complex 2 exhibited more complex reactivity in PBS. Although the major final product was the same as that observed for the aquation in pure water ($^1H$ δ=2.22 ppm), two other minor products were observed by $^1H$ NMR spectroscopy with $CH_3$ proton resonances at 1.91 and 1.56 ppm. Additionally, an intermediate was observed with a $CH_3$ proton resonance at 2.25 ppm.

With the goal of characterizing the aquation and anation products of 2 and 4, the NMR spectra of the free ligands of these complexes in PBS were investigated. Initially, the $^1H$ NMR spectrum of sodium trifluoracetylacetonate, Na(tfac), in PBS displayed a $CH_3$ resonance at 2.25 ppm. Upon further incubation at 37° C. for 6 d, this resonance at 2.25 ppm decayed and was replaced by a major resonance at 2.22 ppm and two minor resonances at 1.91 and 1.56 ppm. Because these signals are the same as those observed during the aquation and anation of 2, without wishing to be bound by theory, the free tfac ligand may be displaced from the platinum center as an intermediate with a chemical shift of 2.25 ppm and then undergoes ligand decomposition reactions. For the ligand of 4,4,4,4-trifluorobenzoylacetone (Htfbz), two peaks in its $^{19}F$ NMR spectrum at −76.37 and −86.7 ppm were initially observed. These two signals possibly correspond to the keto and enol tautomers of the compound. After 6 d at 37° C., the major species in solution was a compound characterized by a singlet in the $^1H$ NMR spectrum at 2.67 ppm and a signal in the $^{19}F$ NMR spectrum at −76.41 ppm. These spectroscopic signals are consistent with the major species observed after the aquation and anation of 4. Thus, as for 2, dissociation from the platinum center may precede causing hydrolytic decomposition of the fluorinated β-diketonate ligand.

Cancer Cell Cytotoxicity.

The antiproliferative activities of 1-5 and cisplatin were determined in HeLa (human cervical cancer), A549 (human lung cancer), U2OS (human osteosarcoma), and MCF-7 (human breast cancer) cell lines by the MTT assay. The cells were treated for a continuous 72 h period. The resulting 50% growth inhibitory concentration ($IC_{50}$) values are summarized in Table 4 and graphically depicted in FIG. 5. Within the four cell lines tested, 1 is the least cytotoxic of the five complexes with $IC_{50}$ values ranging from 24 to 76 μM. The $IC_{50}$ values of complex 3 vary between 7 and 33 μM, indicating that the compounds are slightly more cytotoxic than 1. Complexes 2, 4, and 5 are of comparable cytotoxicities with cisplatin. The $IC_{50}$ values for these compounds are generally less than 10 μM, except for 2 in MCF-7 cells where the $IC_{50}$ is 15 μM.

TABLE 4

$IC_{50}$ Values of 1-5 and Cisplatin in HeLa, A549, U2OS, and MCF-7 Cell Lines and Cellular Uptake in HeLa Cells

| | $IC_{50}$ (μM)[a] | | | | HeLa Cellular Uptake (ng Pt/10$^6$ cells)[b] |
|---|---|---|---|---|---|
| Compound | HeLa | A549 | U2OS | MCF-7 | |
| 1 | 32 ± 5 | 28 ± 9 | 24 ± 2 | 76 ± 2 | 6 ± 2 |
| 2 | 2.9 ± 0.7 | 2.2 ± 0.6 | 4.1 ± 0.8 | 15 ± 2 | 29 ± 9 |
| 3 | 24 ± 4 | 7 ± 2 | 8 ± 2 | 33 ± 6 | 83 ± 8 |
| 4 | 3 ± 1 | 1.3 ± 0.2 | 1.6 ± 0.5 | 4.3 ± 0.3 | 160 ± 20 |
| 5 | 6.7 ± 0.7 | 1.3 ± 0.3 | 2.7 ± 0.7 | 3.1 ± 0.5 | 520 ± 80 |
| cisplatin | 2.1 ± 0.1 | 3.2 ± 0.6 | 5 ± 2 | 14 ± 3 | 14 ± 2 |

[a]The errors are the standard deviations determined from at least three independent experiments.
[b]The errors are determined by error propagation equations..

Figure 5:
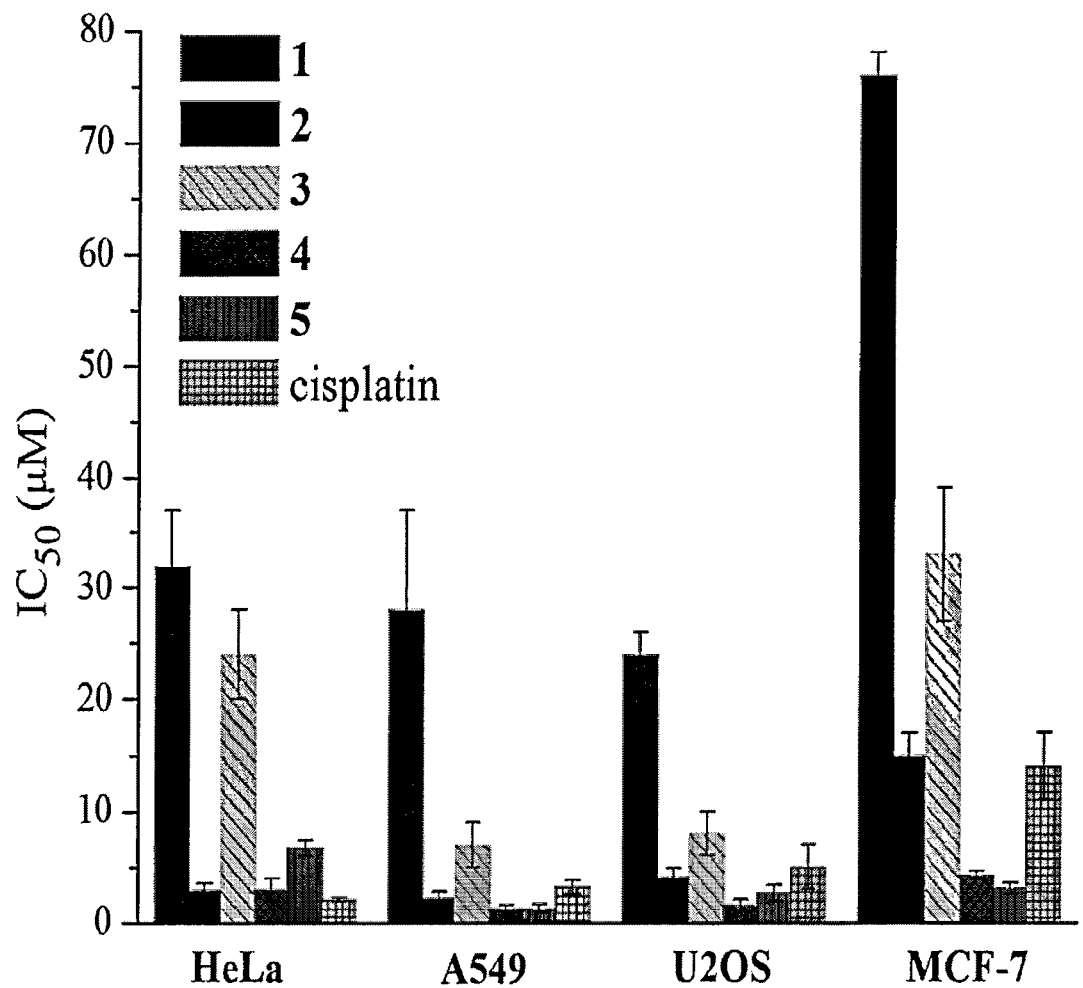
FIG. 5 shows a bar chart representation of the IC$_{50}$ values of cisplatin and some exemplary compounds of the present invention in HeLa, A549, U2OS, and MCF-7 cell lines, according to some embodiments.

In FIG. 5: Bar chart representation of the $IC_{50}$ values of 1-5 and cisplatin in HeLa, A549, U2OS, and MCF-7 cell lines.

Since complex 4 was on average the most cytotoxic of the five complexes, it was submitted to the NCI for evaluation in the NCI-60 tumor cell panel screen. At the NCI, a single-dose cytotoxicity measurement was carried out in 60 cell lines with distinct drug sensitivity profiles. This process can identify drug candidates with unique anticancer spectrums of activity based on which cell lines are sensitive or resistant to the compound of interest. Using the COMPARE algorithm, activity spectrums can be quantitatively correlated with other compounds in the NCI database. Pearson correlation coefficients are used to evaluate similarities in activity spectrums. Correlations coefficients close to one indicate compounds with similar mechanisms of action and resistance profiles. The average cell growth percentage of the 60 cell lines after 48 h treatment with 10 μM of 4 was 89.65%, indicating growth inhibitory action of 4. Compound 4 showed the greatest efficacy in central nervous system (CNS) cancer cell lines, where the average cell growth was 64.52%. Results of the COMPARE algorithm are summarized in Table 5.

TABLE 5

Results of COMPARE Analysis of 4
Compound 4
NSC No. 781186
COMPARE Analysis

| Rank | PCC[a] | NSC No.[b] | Name | Biological Mechanism of Action |
|---|---|---|---|---|
| 1 | 0.589 | 95466 | PCNU | alkylating agent |
| 2 | 0.569 | 750 | busulfan | alkylating agent |
| 3 | 0.559 | 301739 | mitoxantrone | Type II Topoisomerase inhibitor |
| 4 | 0.534 | 355644 | anthrapyrazole | Type II Topoisomerase inhibitor |
| 5 | 0.506 | 178248 | chlorozotocin | alkylating agent |
| 6 | 0.501 | 357704 | cyanomorpholino-ADR | alkylating agent |

TABLE 5-continued

Results of COMPARE Analysis of 4
Compound 4
NSC No. 781186
COMPARE Analysis

| Rank | PCC[a] | NSC No.[b] | Name | Biological Mechanism of Action |
|---|---|---|---|---|
| 7 | 0.495 | 3088 | chlorambucil | alkylating agent |
| 8 | 0.491 | 132313 | dianhydrogalactitol | alkylating agent |
| 9 | 0.489 | 119875 | cisplatin | alkylating agent |
| 10 | 0.485 | 353451 | mitozolamide | alkylating agent |

[a]Pearson correlation coefficient.
[b]Compound identification number utilized by the NCI.

Cellular Uptake.

Figure 6:
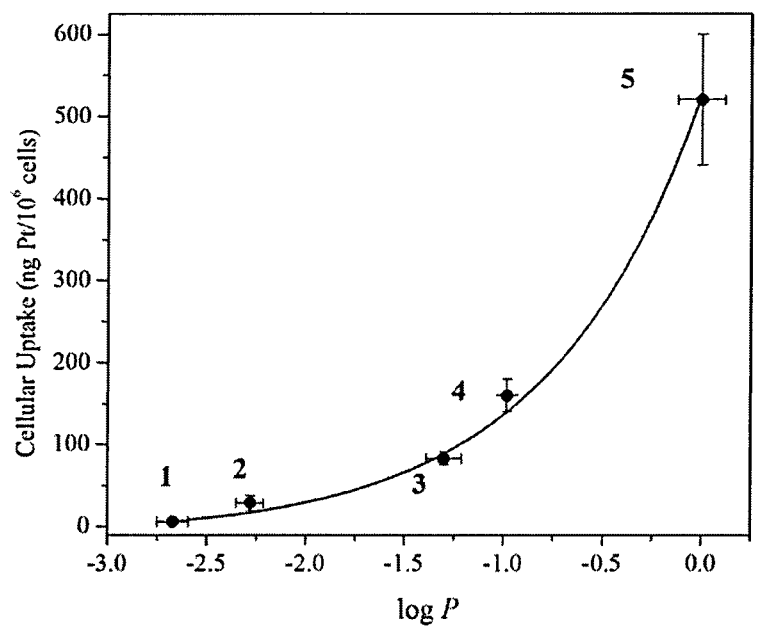
FIG. 6 shows a plot of complex log P values versus cellular uptake, according to some embodiments.

The cellular uptake of cisplatin and 1-5 by HeLa cells after 4 h exposure at 10 μM concentration was measured using graphite furnace atomic absorption spectroscopy (GFAAS). The results are tabulated in Table 3. The cellular uptake scales with the lipophilicity of the compound in an exponential fashion (FIG. 6). The most lipophilic complex, 5, is taken up to the largest extent (520±80 ng Pt/10$^6$ cells), whereas the least lipophilic complex is taken up to the least extent (6±2 ng Pt/10$^6$ cells). All complexes except 1 have a larger accumulation in HeLa cells than cisplatin under similar conditions.

In FIG. 6: Plot of complex log P values versus cellular uptake. The line is an exponential fit of the data.

Intracellular DNA Platination.

Because platinum-based drugs exert their cytotoxic effects by the formation of DNA cross-links, the extent to which 1-5 bind to intracellular DNA was measured. Cells were treated with 100 μM of the platinum complexes for 4 h and then incubated for an additional 16 h in platinum-free growth medium. The nuclear DNA was isolated, and the quantity of bound platinum was measured by GFAAS. The results of this study are shown in Table 6. The extent of DNA platination follows the order 5≈4>cisplatin>3≈2>1.

TABLE 6

Intracellular DNA Platination in HeLa Cells Induced by Cisplatin and 1-5[a]

| Compound | Pt/DNA (pmol/μg) |
|---|---|
| cisplatin | 1.58 ± 0.97 |
| 1 | 0.063 ± 0.012 |
| 2 | 0.30 ± 0.07 |
| 3 | 0.35 ± 0.24 |
| 4 | 14 ± 3 |
| 5 | 23 ± 10 |

[a]Reported errors are the standard deviations from at least three experiments.

Discussion

This study was conducted to systematically investigate the physical properties and anticancer efficacies of a small set of β-diketonato cis-diammineplatinum(II) complexes. The five β-diketonate ligands chosen for this study were systematically varied by addition of either a phenyl ring or a trifluoromethyl group (FIGS. 1c-g). Such variations enabled the investigation of how alterations of the hydrophobicity and electron-withdrawing properties of the leaving group ligand translated into different anticancer efficacies in vitro.

The three synthetic methodologies employed for the preparation of 1-5 are shown in FIG. 2. For the synthesis of 1 and 2, the sulfate salt of the cis-diamminediaquaplatinum(II) cation was utilized. The treatment of this cation with Ba(acac)$_2$ or Ba(tfac)$_2$ afforded BaSO$_4$ as an insoluble white solid and 1 or 2, which were subsequently isolated from the aqueous solution. For the synthesis of 3 and 4, the nitrate salt of the cis-diamminediaquaplatinum(II) cation was treated with Na(bzac) or Na(tfbz). The NaNO$_3$ byproduct of the reaction could be washed away using cold water with little product loss since 3 and 4 are only sparingly soluble in water. The low solubility of the ligand Hdbm in water necessitated the use of N,N-dimethylformamide (DMF) as the solvent. Activation of cisplatin in DMF with AgNO$_3$ followed by the treatment of Na(dbm) afforded 5 after the appropriate reaction workup albeit it lower yields. The preparation of the analogous hexafluoroacetylacetonate (hfac) complex was attempted as well. Without wishing to be bound by theory, the difficulties associated with obtaining this complex may arise from the lability of the strongly electron-withdrawing hfac ligand.

Characterization data obtained by ESI-MS, elemental analysis, IR spectroscopy, and multinuclear NMR spectroscopy were consistent with the proposed structures and elemental compositions of 1-5. Of particular relevance are the $^{195}$Pt NMR chemical shifts of the complexes. The $^{195}$Pt NMR chemical shift is very sensitive to the coordination environment of the metal center and can span a region of over 13,000 ppm. Here, the $^{195}$Pt NMR chemical shifts of 1-5 spanned a region of 139 ppm (Table 1), indicating that the peripheral substituents on the β-diketonate ligands may influence the electron density at the platinum center. Complex 1 has the most shielded Pt nucleus, which resonates at −1593 ppm, whereas 4 has the most deshielded center, which resonates at −1454 ppm. The chemical shift for this class of compounds appears to be at least partially dependent on the electron withdrawing strength of the ligand. The trifluoromethyl substituents of 2 and 4 deshield the Pt nucleus by approximately 100 ppm relative to their analogues, 1 and 3, without the trifluoromethyl groups. The phenyl groups of 3, 4, and 5 also deshield the Pt nucleus, but to a lesser extent than the trifluoromethyl groups. Compared to their analogues without phenyl groups, 3, 4, and 5 are deshielded by 20-44 ppm. The X-ray crystal structures of 3 and 4 display the expected coordination geometries (FIG. 3). The complexes are structurally analogous and display comparable interatomic distances and angles (Table 2).

An important physical property that may affect the biodistribution of a drug candidate is its lipophilicity. The lipophilicity of a compound is quantitatively evaluated by its log P values, where P is the water-octanol partition coefficient. More positive log P values correspond to more lipophilic complexes, whereas more negative log P values correspond to more hydrophilic complexes. The log P values for cisplatin and 1-5 are given in Table 3 and FIG. 4. The addition of lipophilic groups to the β-diketonate ligands increased the log P values of the resulting complex. Thus, the lipophilicity can be tuned with the appropriate use of functional groups. For comparison, the log P values of the free ligands in the keto form were computed with an online program. A linear correlation between the calculated log P values of the ligands and the experimentally measured log P values of the complexes exists, as shown in FIG. 4. The slope of the best fit line is 0.90. This value, which is close to 1, indicates that coordination of the β-diketonate ligand to the cis-diammineplatinum(II) moiety affected the lipophilicity in an additive fashion and is consistent with the additive properties of substituent hydrophobicity constants. The intercept of the best fit line gives rise to a values of −2.8, which can be interpreted as the substituent hydrophobicity constant for the [Pt(NH$_3$)$_2$]$^+$ in this class of compounds.

After establishing that different substituents on the β-diketonate ligands have a significant effect on the lipophilicities of 1-5, the role of these substituents on modulating the reactivities of the complexes was investigated. The stabilities of 1-5 in water and pH 7.4 phosphate buffered saline at 37° C. were assessed by NMR spectroscopy. In either water or PBS, no sign of decomposition was observed for 1, 3, and 5 for up to 25 days. Compounds 2 and 4 decomposed in water with half-lives of 58 and 29 days, respectively, and in PBS with half-lives of 3.4 and 1.8 days, respectively. The observation that the non-fluorinated complexes, 1, 3, and 5, appear to have an indefinite lifetime in water and aqueous buffer indicate that the strongly electron-withdrawing properties of the trifluoromethyl groups in 2 and 4 may be responsible for the increased reactivities of these complexes. In this context, however, it should be noted that 2 and 4 are still significantly more inert than cisplatin, which has an aqueous half-life of 2 h. In PBS, which contained 137 mM NaCl and 10 mM $HPO_4^{2-}$, the half-lives of 2 and 4 decreased to 3.4 days and 1.8 days indicating that the high ion concentration may play a role in their reactivities. Carboplatin, which exhibits no decomposition for up 60 days in water, displays increased reactivity in the presence of high phosphate and chloride ion concentration that proceeds by direct anion attack at the complex and without an aquated intermediate. A similar process may explain the increased rates of decomposition of 2 and 4 in PBS relative to pure water.

The cell-killing abilities of the complexes were assessed in four human cancer cell lines. $IC_{50}$ values are displayed in Table 4 and graphically compared in FIG. 5. The general trend of cytotoxicity, among the four cell lines, follows the order: 1<3<2≈4≈5. Compounds 2, 4, and 5 have $IC_{50}$ values comparable to or lower than those of cisplatin. The differences in observed cytotoxicities among the five complexes may be attributed to variations in the lipophilicity and reaction kinetics conferred by the β-diketonate leaving group ligands since the DNA-binding cis-diammineplatinum(II) fragment is the same in all five complexes and cisplatin.

The cellular uptake properties of the five complexes and cisplatin were measured in HeLa to see whether this parameter might be the dominant factor in determining cytotoxicity. The results are summarized in Table 4. As shown in FIG. 4, the cellular uptake is a function of lipophilicity of the platinum complex. This correlation suggests that these complexes are dependent on a passive diffusion uptake mechanism. Given that these complexes are cations, they may also take advantage of organic cation transporters for selective transport into cancer cells, like oxaliplatin. No correlation, however, was observed between the cellular uptakes and $IC_{50}$ values of the five complexes. This result indicates that the reaction kinetics of the complexes may also play a role in their biological activities. Consistent with this hypothesis is the observation that the fluorinated complexes, 2 and 4, exhibited comparable or better cytotoxicities than 5 despite the fact that over two times the amount of 5 is taken up by cells. The increased reactivities of 2 and 4 in water and buffer may be the reasons why they exhibited comparable cytotoxicity to 5 even though they are present in significantly lower concentrations within the cell. A similar correlation between aquation rates and activity was observed in a series of carboplatin derivatives bearing fluorinated CBDCA leaving group ligands. Rapid aquation of the fluorinated CBDCA ligands relative to the non-fluorinated ligands is observed and may be responsible for the increased cytotoxic activity of the fluorinated derivates relative to underivatized carboplatin.

The amount of platinum found on the DNA of HeLa cells treated with cisplatin and 1-5 (Table 6) was not directly correlated with the $IC_{50}$ values of the complexes, although the least active complex, 1, does induce the least amount of DNA platination. However, for determination of the $IC_{50}$ values the cells were treated for a continuous 72 h period, whereas for the DNA platination measurements, cells were treated at a high concentration for 4 h and then allowed to incubate for an additional 16 h in the absence of platinum. During this 16 h post-treatment period, efflux of platinum complexes out of the cell might become an important factor. Additionally, cellular targets other than DNA could modulate the cytotoxic activities of 1-5. The balance between lipophilicity and reactivity in the formation of Pt-DNA adducts is still apparent, however. Complexes 2 and 3 platinate DNA to a similar extent (≈0.3 pmol Pt/μg DNA), as do complexes 4 and 5 (14-23 pmol Pt/μg DNA). Cellular accumulation studies indicate that 3 and 5 are taken up to a much greater extent than 2 and 4, which may be due to their greater lipophilicities. The similar DNA platination levels of these complexes may reflect the higher reactivities of the fluorinated complexes 2 and 4, which may compensate for their lower intracellular abundance.

Figure 7:
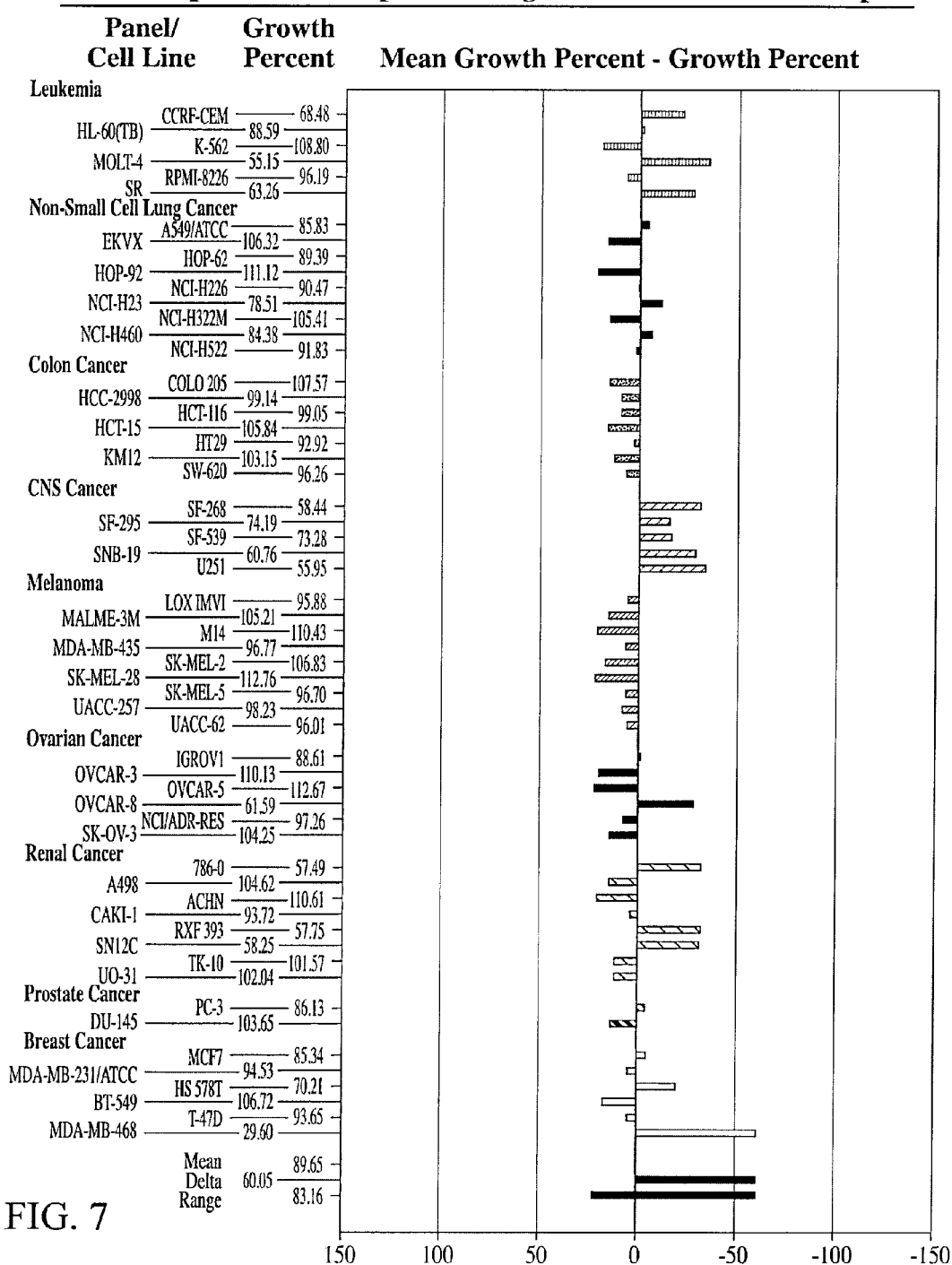
FIG. 7 shows results from an NCI-60 tumor cell panel screen of an exemplary compound of the present invention, according to some embodiments.

Among the compounds studied, 4 appeared to have a balance of lipophilicity and reactivity. The average $IC_{50}$ value of this complex in the four cells lines tested is 2.6 μM and is the lowest among the five complexes tested. For this reason, complex 4 was submitted to the NCI for testing in the NCI-60 tumor cell panel screen. As described above, the NCI-60 tumor cell panel screen utilizes 60 different cell lines with distinct sensitivity profiles and measures the cell growth inhibitory action of a compound of interest at a single dose. Differential cell growth inhibition among the 60 cell lines indicates the compounds spectrum of activity, which can be quantitatively compared to the other compounds in the NCI database via the COMPARE algorithm. For 4, the average cell growth percent among the 60 cell lines after a single dose (10 μM) treatment was 89.65% relative to the complex-free control (FIG. 7). The apparent lower activity of 4 in the NCI-60 tumor cell screen compared to that observed may be the result of different experimental conditions. The shorter incubation time (48 h), the use of RPMI as culture medium, different initial cell densities, and use of the sulforhodamine B (SRB) assay by the NCI screen may contribute to the discrepancy. In fact, higher $IC_{50}$ values are typically measured with the SRB assay compared to the MTT assay since the SRB assay measures total protein content instead of mitochondrial activity. The COMPARE algorithm was utilized to investigate how the spectrum of activity of 4 matches those of other anticancer agents in the NCI database. A table displaying the ten anticancer compounds with the highest correlation coefficients with the spectrum of activity of 4 is found in Table 5. Eight of these ten compounds are known DNA alkylating agents. Cisplatin is one of the top ten with a correlation coefficient of 0.489. These correlations indicate that 4 and the related β-diketonato complexes act by binding DNA, with the β-diketonate ligands serving as the leaving groups. The relatively high correlation with the activity of cisplatin is consistent with formation of similar DNA cross-links. The Pearson correlation coefficient comparing the spectrum of activity of cisplatin and carboplatin is 0.798 and is therefore much greater than that for 4 and cisplatin. The β-diketonate ligand of 4 apparently has a larger influence on the cell line selectivity than the CBDCA ligand of carboplatin.

A systematic study of the physical properties and in vitro anticancer efficacy of a series of cis-diammineplatinum(II) complexes with β-diketonate leaving group ligands has been described. The results indicate that modifications of the β-diketonate ligands can affect both the lipophilicity and reactivity of the resulting platinum complex. The lipophilicity of these compounds may be important because it can affect the degree of cellular uptake, whereas optimal reactivity kinetics may ensure that a significant amount of platinum can bind to DNA or other cellular targets within the biological time frame. Of the compounds presented here, complex 4 exhibited the highest cytotoxicity on average. The trifluorobenzoylacetonate (tfbz) ligand of 4 carries both a phenyl and trifluoromethyl group. These two groups appear to provide an desirable combination of lipophilicity and reactivity for biological activity. As expected, the NCI-60 tumor cell screen revealed 4 to have a similar spectrum of activity as other alkylating agents including cisplatin. Carboplatin, which also has a similar spectrum of activity as cisplatin, has been used as a less toxic alternative.

Experimental Section

Materials and Methods.

All syntheses were carried out under normal atmospheric conditions without the exclusion of oxygen or moisture. Cisplatin and $Ba(acac)_2 \cdot H_2O$ were purchased from Strem Chemicals and used as received. The β-diketonate ligands were purchased from Alfa Aesar and used as received. Distilled water and analytical grade DMF were used for reactions. The purities (>95%) of the newly synthesized compounds were verified by the absence of unidentified peaks in the $^1H$ NMR spectra and by elemental analyses.

Physical Measurements.

NMR measurements were recorded on a Bruker DPX-400 spectrometer in the MIT Department of Chemistry Instrumentation Facility at 20° C. unless otherwise stated. $^1H$ and $^{13}C\{^1H\}$ NMR spectra were referenced internally to residual solvent peaks and chemical shifts are expressed relative to tetramethylsilane, $SiMe_4$ (δ=0 ppm). $^{195}Pt\{^1H\}$ and $^{19}F\{^1H\}$ NMR spectra were referenced externally using standards of $K_2PtCl_4$ in $D_2O$ (δ=−1628 ppm relative to $Na_2PtCl_6$) and trifluorotoluene (δ=−63.72 ppm relative to $CFCl_3$), respectively. Fourier transform infrared (FTIR) spectra were recorded with a ThermoNicolet Avatar 360 spectrophotometer running the OMNIC software. Samples were prepared as KBr disks. Electrospray ionization mass spectrometry (ESI-MS) measurements were acquired on an Agilent Technologies 1100 series LC-MSD trap. Graphite furnace atomic absorption spectrometry was carried out using a Perkin Elmer AAnalyst600 GFAAS. Elemental analyses were performed by a commercial analytical laboratory.

Synthesis of $[Pt(acac)(NH_3)_2](SO_4)_{0.5}$ (1)

A suspension of cisplatin (0.500 g, 1.67 mmol) and $Ag_2SO_4$ (0.499 g, 1.60 mmol) in 15 mL of water was stirred at room temperature in the dark for 12 h. The resulting suspension was filtered to remove white AgCl and, to the filtrate, a 10 mL aqueous solution of $Ba(acac)_2 \cdot H_2O$ (0.268 g, 0.800 mmol) was added dropwise, inducing the precipitation of insoluble $BaSO_4$. This suspension was stirred at room temperature for 3 h and then filtered. The orange-brown filtrate was concentrated to dryness under reduced pressure at 60° C. to afford a brown residue. The residue was dissolved in 5 mL of MeOH at 65° C. and filtered through Celite to remove an insoluble impurity. Treatment of this MeOH solution with 15 mL of $Et_2O$ yielded the desired compound as a white solid which was isolated by centrifugation and washed an additional two times with 10 mL of $Et_2O$ before drying in vacuo. Yield: 0.438 g (70%). M.p. >140° C. (gradual darkening and decomposition). $^1H$ NMR (400 MHz, MeOD-$d_4$): δ 5.58 (s, 1H), 1.85 (s, 6H). $^{13}C\{^1H\}$ NMR (100 MHz, MeOD-$d_4$): δ 185.6, 103.3, 26.1. $^{195}Pt\{^1H\}$ NMR (86 MHz, MeOD-$d_4$): δ −1593. IR (KBr, cm$^{-1}$): 3446 m, 3179 s, 3134 s, 3075 m, 1564 s, 1525 vs, 1427 w, 1382 m, 1331 w, 1304 w, 1284 w, 1194 w, 1112 vs, 1024 w, 951 w, 938 w, 869 w, 831 w, 772 vw, 659 m, 619 m, 541 w, 480 w. ESI-MS (pos. ion mode, MeOH): m/z 328.1 ([M]$^+$, calcd. 328.1). Anal. Calcd. for 1, $C_5H_{13}N_2O_4PtS_{0.5}$: C, 15.96; H, 3.48; N, 7.44. Found: C, 15.82; H, 3.51; N, 6.94.

Synthesis of $[Pt(tfac)(NH_3)_2](SO_4)_{0.5}$ (2)

A suspension of cisplatin (0.500 g, 1.67 mmol) and $Ag_2SO_4$ (0.499 g, 1.60 mmol) in 15 mL of water was stirred at room temperature in the dark for 12 h. The resulting suspension was filtered to remove white AgCl and, to the filtrate, a 10 mL hot (70° C.) aqueous solution of $Ba(OH)_2 \cdot 8H_2O$ (0.252 g, 0.800 mmol) and Htfac (0.246 g, 1.60 mmol) was added dropwise, inducing the precipitation of insoluble $BaSO_4$. The yellow suspension was stirred at room temperature for 3 h and then filtered. The bright yellow filtrate was concentrated to dryness under reduced pressure at 60° C. to afford the desired compound as a yellow solid. The yellow solid was resuspended in 5 mL of cold $H_2O$, filtered, and washed sequentially with 5 mL of cold $H_2O$ and twice with 5 mL of $Et_2O$ before being dried in vacuo. Yield: 0.314 g (44%). M.p. >190° C. (gradual darkening and decomposition). $^1H$ NMR (400 MHz, MeOD-$d_4$): δ 6.10 (s, 1H), 2.00 (s, 3H). $^{19}F\{^1H\}$ NMR (376 MHz, MeOD-$d_4$): δ −76.43. $^{195}Pt\{^1H\}$ NMR (86 MHz, MeOD-$d_4$): δ −1497. IR (KBr, cm$^{-1}$): 3341 m, 3101 s, 2917 w, 1592 s, 1526 m, 1458 w, 1367 w, 1304 vs, 1240 m, 1194 m, 1138 vs, 876 w, 805 w, 743 w, 668 w, 618 m, 448 w. ESI-MS (pos. ion mode, MeOH): m/z 382.0 ([M]$^+$, calcd. 382.0). Anal. Calcd. for 2, $C_5H_{10}F_3N_2O_4PtS_{0.5}$: C, 13.96; H, 2.34; N, 6.51. Found: C, 13.81; H, 2.48; N, 6.41.

Synthesis of $[Pt(bzac)(NH_3)_2](NO_3)$ (3)

A mixture of cisplatin (0.500 g, 1.67 mmol) and $AgNO_3$ (0.553 g, 3.25 mmol) in 10 mL of water were stirred together in the absence of light for 12 h at room temperature. The resulting suspension was filtered to remove white AgCl and a hot aqueous solution (70° C., 10 mL) of Hbzac (0.264 g, 1.63 mmol) and NaOH (0.065 g, 1.6 mmol) was added dropwise to the filtrate, forming a yellow suspension, which was left to stir at room temperature for 4 h. The mixture was concentrated in vacuo at 60° C. to a volume of 8 mL and then filtered to collect the desired compound as a pale yellow solid. This solid was suspended in 10 mL of $Et_2O$ and isolated by centrifugation twice to remove an ether-soluble impurity, before being dried in vacuo. Yield: 0.400 g (53%). M.p. 160° C. (gradual darkening), 210-215° C. (dec). $^1H$ NMR (400 MHz, MeOD-$d_4$): δ 7.95 (d, 2H), 7.55 (t, 1H), 7.41 (app t, 2H), 6.31 (s, 1H), 2.00 (s, 3H). $^{13}C\{^1H\}$ NMR (100 MHz, MeOD-$d_4$): δ 187.5, 178.2, 138.0, 132.7, 129.9, 128.4, 100.3, 26.7. $^{195}Pt\{^1H\}$ NMR (86 MHz, MeOD-$d_4$): δ −1572. IR (KBr, cm$^{-1}$): 3435 w, 3279 s, 3200 m, 3116 m, 1599 w, 1584 m, 1548 s, 1514 vs, 1490 m, 1451 m, 1397 s, 1383 s, 1341 vs, 1312 vs, 1221 w, 957 w, 878 w, 779 m, 713 m, 689 w, 671 w, 580 vw, 483 vw. ESI-MS (pos. ion mode, MeOH): m/z 390.1 ([M]$^+$, calcd. 390.1), 842.0 ([2M+$NO_3$]$^+$, calcd. 842.1). Anal. Calcd. for 3, $C_{10}H_{15}N_3O_5Pt$: C, 26.55; H, 3.34; N, 9.29. Found: C, 26.30; H, 3.26; N, 9.20.

Synthesis of $[Pt(tfbz)(NH_3)_2](NO_3)$ (4)

A mixture of cisplatin (0.500 g, 1.67 mmol) and $AgNO_3$ (0.553 g, 3.25 mmol) in 10 mL of water were stirred together in the absence of light for 12 h at room temperature. The resulting suspension was filtered to remove white AgCl, and a hot aqueous solution (70° C., 10 mL) of Htfbz (0.352 g, 1.63 mmol) and NaOH (0.065 g, 1.6 mmol) was added dropwise to the filtrate, forming a bright yellow suspension, which was left to stir at room temperature for 4 h. The mixture was then concentrated to dryness under reduced pressure at 60° C. to afford an orange residue. The residue was dissolved in 10 mL acetone and filtered to remove $NaNO_3$ byproduct. On top of the bright yellow filtrate, 10 mL of $Et_2O$ was carefully layered, and overnight bright yellow crystals of the desired compound formed. The supernatant was decanted and the crystals were washed with 5 mL of cold water to remove a white solid impurity, followed by 5 mL of $Et_2O$ prior to drying in vacuo. Yield: 0.215 g (25%). M.p. >230° C. (gradual darkening and decomposition). $^1$H NMR (400 MHz, MeOD-$d_4$): δ 8.07 (d, 2H), 7.71 (t, 1H), 7.50 (app t, 2H), 6.72 (s, 1H). $^{13}$C{$^1$H} NMR (100 MHz, MeOD-$d_4$): δ 184.2, 166.9 (q, $^2J_{CF}$=34 Hz), 137.0, 134.6, 130.5, 128.9, 119.3 (q, $^1J_{CF}$=282 Hz), 96.5. $^{19}$F{$^1$H} NMR (376 MHz, MeOD-$d_4$): δ −76.17. $^{195}$Pt{$^1$H} NMR (86 MHz, MeOD-$d_4$): δ −1454. IR (KBr, cm$^{-1}$): 3431 m, 3342 m, 3213 m, 1592 s, 1564 vs, 1536 s, 1490 w, 1458 w, 1420 m, 1384 s, 1326 s, 1303 vs, 1259 m, 1203 s, 1137 s, 1024 w, 948 w, 813 w, 776 m, 697 s, 619 w, 572 w. ESI-MS (pos. ion mode, MeOH): m/z 444.1 ([M]$^+$, calcd. 444.0), 950.1 ([2M+$NO_3$]$^+$, calcd. 950.1). Anal. Calcd. for 4, $C_{10}H_{12}F_3N_3O_5Pt$: C, 23.72; H, 2.39; N, 8.30. Found: C, 23.75, H, 2.36, N, 8.41.

Synthesis of [Pt(dbm)(NH$_3$)$_2$](NO$_3$) (5)

Cisplatin (750 mg, 2.50 mmol) and $AgNO_3$ (828 mg, 4.87 mmol) were stirred in 6 mL of DMF at room temperature for 12 h in the absence of light. The resulting suspension was filtered to remove AgCl. The pale yellow filtrate was added dropwise to $Na_2CO_3$ (321 mg, 3.00 mmol) and Hdbm (560 mg, 2.50 mmol) in 5 mL of DMF. This mixture was stirred at room temperature for 3.5 h and then filtered. The filtrate was concentrated to dryness under vacuum at 60° C. to obtain an orange oily residue. This residue was dissolved in 10 mL of MeOH and filtered. The addition of $Et_2O$ (40 mL) afforded the desired product as a yellow solid, which was isolated by filtration, washed with cold $H_2O$ (4° C., 20 mL) and $Et_2O$ (20 mL), and dried under vacuum. Yield: 0.306 g (24%). M.p. 221-229° C. (dec). $^1$H NMR (400 MHz, MeOD-$d_4$): δ 8.07 (d, 4H), 7.60 (t, 2H), 7.47 (t, 4H), 6.96 (s, 1H). $^{13}$C{$^1$H} NMR (100 MHz, MeOD-$d_4$): δ 179.9, 138.5, 132.9, 130.0, 128.4, 97.5. $^{195}$Pt{$^1$H} NMR (86 MHz, MeOD-$d_4$): δ −1528. IR (KBr, cm$^{-1}$): 3438 m, 3278 m, 3198 m, 3058 w, 1589 m, 1530 vs, 1487 s, 1454 m, 1385 s, 1318 s, 1237 m, 1075 w, 1024 w, 999 w, 945 w, 827 w, 757 m, 706 m, 670 m, 596 vw, 559 vw. ESI-MS (pos. ion mode, MeOH): m/z 452.0 ([M]$^+$, calcd. 452.1), 965.8 ([2M+$NO_3$]$^+$, calcd. 966.2). Anal. Calcd. for 5.$H_2O$, $C_{15}H_{19}N_3O_6Pt$: C, 33.84; H, 3.60; N, 7.89. Found: C, 34.17; H, 3.24; N, 7.99.

X-Ray Crystallography.

Vapor diffusion of diethyl ether into methanol solutions afforded single crystal of 3 and 4. The single crystals were mounted in Paratone oil on a cryoloop and frozen under a 110 K or 100 K KRYO-FLEX nitrogen cold stream. Data were collected on a Bruker APEX CCD X-ray diffractometer with graphite-monochromated Mo—Kα radiation (λ=0.71073 Å) controlled by the APEX2 software package. Absorption corrections were applied using SADABS. The structures were solved using direct methods and refined on $F^2$ with the SHELXTL-97 software package. Structures were checked for higher symmetry using PLATON. All non-hydrogen atoms were located and refined anisotropically. Hydrogen atoms were placed in idealized locations and given isotropic thermal parameters equivalent to either 1.5 (terminal $CH_3$ or $NH_3$ hydrogen atoms) or 1.2 times the thermal parameter of the atom to which they were attached. Crystallographic data collection and refinement parameters (Table S1, SI) and cif files can be found in the elsewhere. The cif files of 3 and 4 have also been deposited in the Cambridge Crystallographic Data Centre (http://www.ccdc.cam.ac.uk/) under the accession numbers 868860 and 868861, respectively.

Solution Stability Measurements.

The platinum complexes were dissolved in water or pH 7.4 PBS containing 10% $D_2O$ to a typical concentration of 1 mM. The solutions were transferred to NMR tubes and incubated in a 37° C. water bath. $^1$H and $^{19}$F NMR spectra were obtained at various type points during the incubation. A small amount of 1,4-dioxane (δ=3.75 ppm) was included in the samples as an internal standard for referencing the $^1$H NMR spectra and a sealed capillary containing aqueous KF (δ=−120.46 ppm) was used for referencing $^{19}$F NMR spectra. The methyl group of 2 in the $^1$H NMR spectra was integrated relative to the 1,4-dioxane reference at different time points and used for kinetic analyses. The trifluoromethyl group of 4 in the $^{19}$F NMR spectra was integrated relative to the KF standard at different time points and used for kinetic analyses. Under the assumption of first-order kinetics, approximate half-lives were determined by fitting a line to a plot of ln [Pt] versus time and using the integrated first-order rate law, ln [Pt]=−kt+[Pt]$_o$ and the relationship, $t_{1/2}$=ln 2/k, where [Pt]$_o$ is the starting concentration of complex, k is the pseudo first-order rate constant, t is time, and $t_{1/2}$ is the half-life. Water suppression for $^1$H NMR spectra was accomplished with presaturation. The pH of the solutions was measured at the beginning and end of the desired incubation time using a DG-111-SG glass electrode calibrated with standard buffers.

Partition Coefficient Measurements.

Water or PBS were stirred with octanol for 24 h and then centrifuged for 5 min to obtain octanol-saturated water and water-saturated octanol. The platinum complexes were dissolved in the octanol-saturated water, or PBS for cisplatin, to a typical concentration of 0.03 to 3 mM and then mixed with water-saturated octanol in volumetric ratios of 1:1, 1:2, and 2:1 in duplicate. The mixtures were vortexed for 0.5 h and then centrifuged for 5 min. The layers were separated carefully using a fine-gauge needle and then analyzed for Pt content by GFAAS. The partition coefficient was taken as ratio of the concentration of platinum in the octanol layer to that in the aqueous layer (P=$c_{oct}/c_{water}$). The reported error is the standard deviation of the six measurements obtained from this protocol.

Calculated ligand log P values were obtained from the online program ALOGPS 2.1 available at the Virtual Computational Chemistry Laboratory. Only the keto tautomeric form of the protonated ligand was used for these calculations. In addition to using the ALOGPS algorithm, this program also calculates log P values using several other algorithms for comparison. The values presented here are the average log P values computed for all the algorithms and the errors reported is the standard deviation of these values.

Cell Lines and Culture Conditions.

HeLa (human cervical cancer), A549 (human lung cancer), U2OS (osteosarcoma), MCF-7 (human breast cancer) cells were grown as adherent monolayers in growth medium consisting of Dulbecco's Modified Eagle Medium (DMEM) supplemented with 10% fetal bovine serum (FBS) and 1% penicillin/streptomycin. The cultures were grown in 25 cm$^2$ flasks in an incubator at 37° C. with a humidified atmosphere composed of 5% $CO_2$.

Cytotoxicity Assays.

The colorimetric MTT assay was used determine the cytotoxicity of cisplatin and the β-diketonate platinum complexes. Trypsinized cells were seeded into a 96-well plate at a cell density of 2000 cells/well in 200 μL of growth medium and incubated for 24 h. The medium was then removed and 200 μL new growth medium containing various concentrations of the platinum complexes was added. After 72 h, the medium was removed, 200 μL of a 0.8 mg/mL solution of MTT in DMEM was added, and the plate was incubated further for 4 h. The DMEM/MTT mixture was aspirated and 200 μL of DMSO with 10% pH 10.5 glycine buffer was added to dissolve the resulting purple formazan crystals. The absorbance of the plates was read at 555 nm. Absorbance values were normalized to the platinum-free control wells and plotted as [Pt] versus % viability. $IC_{50}$ values were interpolated from the resulting curves. The reported $IC_{50}$ values are the averages from at least three independent experiments, which each consisted of six replicates per concentration level. Dilutions of the platinum complexes in growth medium were made from concentrated (1-3 mM) solutions in distilled water for β-diketonate platinum complexes or pH 7.4 PBS for cisplatin.

Compound 4 was submitted to the NCI in July 2011 for single-dose testing in the NCI-60 tumor cell screen. These tests were carried out by the NCI using their established protocols. FIG. 7 shows the results from NCI-60 tumor cell panel screen of 4.

Cellular Uptake Studies.

The total platinum uptake per cell was determined using slight modifications of a previously described protocol. In two 6-well plates, $3 \times 10^5$ cells per well were seeded in 3 wells with 2.5 mL of growth medium. In one of the plates, the additional 3 wells were filled with 2.5 mL of growth medium to act as blanks for non-specific platinum adsorption on the surface of the well. After incubating for 48 h, each well in the plate containing both cells and cell-free medium was treated with 0.278 mL of a 100-μM solution of the desired compound to give an exposure concentration of 10 μM. The cells and cell-free blanks were incubated with the Pt complex for 4 h. Meanwhile, the cells in the other plate were counted with trypan blue after detachment with trypsin in order to obtain the number of cells per well. After the 4 h incubation period, the growth medium was aspirated and all six wells were washed twice with 3 mL of pH 7.4 PBS and then treated with exactly 0.5 mL of hot (≈90° C.) concentrated nitric acid for 2 h. This nitric acid was analyzed by GFAAS to determine the total Pt content per well. The amount of Pt per cell was calculated by subtracting the average amount of Pt found in the blank wells from the average amount of Pt found in the cell-containing wells and normalizing to the average number of cells per well.

Intracellular DNA Platination Measurements.

Five million HeLa cells were seeded in a 100 mm Petri dish containing 9 mL of growth medium. On the following day, the cells were treated with the platinum complex at 100 μM concentration for 4 h. The growth medium was then replaced with platinum-free medium, and the cells were incubated for an additional 16 h. Cells, both floating and attached, were collected and combined. Trypsin (2 mL) was used to detach the cells. The combined cells were centrifuged for 5 min at 4° C., and the resulting cell pellet was washed twice with 3 mL of ice-cold PBS. DNAzol (1 mL, genomic DNA isolation reagent, MRC), containing 100 μg/mL RNase A, was used to lyse the cell pellet. DNA was precipitated with 0.5 mL of absolute ethanol, washed 2 times with 75% ethanol (0.75 mL), and redissolved in 200 μL of 8 mM NaOH. The DNA concentration was determined by UV-visible spectroscopy, and platinum was quantified by GFAAS. The reported values are the average of at least three independent experiments with the error reported as the standard deviation.

Whereas several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A compound having the structure:

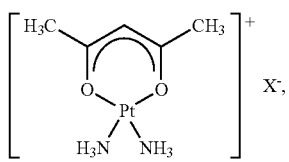
(I)

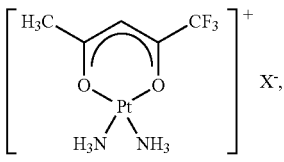
(II)

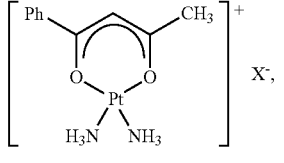
(III)

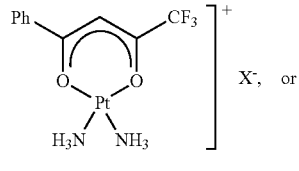
(IV) or

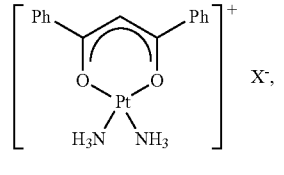
(V)

wherein $X^-$ is a counterion.

2. A compound having the structure:

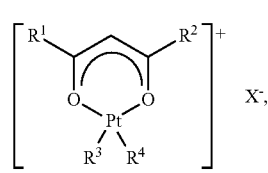
(VI)

wherein:
$R^1$ and $R^2$ are independently selected from the group consisting of alkyl optionally substituted, heteroalkyl optionally substituted, and aryl optionally substituted, provided at least one of $R^1$ or $R^2$ is not alkyl or haloalkyl;
$R^3$ and $R^4$ are independently selected from the group consisting of ammonia, an optionally substituted heterocycle including at least one nitrogen, and an optionally substituted amine, or $R^3$ and $R^4$ can be joined together to form a bidentate ligand;
and
$X^-$ is a counterion.

3. A compound having the structure:

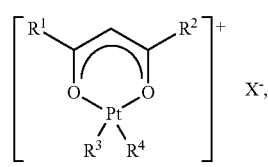
(VII)

wherein:
$R^1$ and $R^2$ are independently selected from the group consisting of alkyl optionally substituted, heteroalkyl optionally substituted, and aryl optionally substituted, provided at least one of $R^1$ or $R^2$ is aryl optionally substituted;
$R^3$ and $R^4$ are independently selected from the group consisting of ammonia, an optionally substituted heterocycle including at least one nitrogen, and an optionally substituted amine, or $R^3$ and $R^4$ can be joined together to form a bidentate ligand;
and
$X^-$ is a counterion.

4. A compound having the structure:

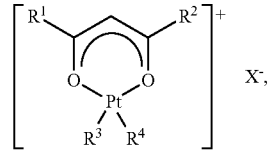
(VIII)

wherein:
$R^1$ and $R^2$ are independently selected from the group consisting of alkyl optionally substituted, heteroalkyl optionally substituted, and aryl optionally substituted; and
$R^3$ and $R^4$ are independently selected from the group consisting of ammonia an optionally substituted heterocycle including at least one nitrogen, and an optionally substituted amine;
$X^-$ is a counterion.

5. A compound having the structure:

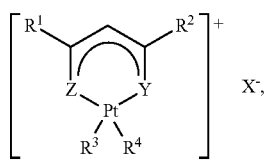

wherein:
$R^1$ and $R^2$ are independently selected from the group consisting of alkyl optionally substituted, heteroalkyl optionally substituted, and aryl optionally substituted;
$R^3$ and $R^4$ are independently selected from the group consisting of ammonia, an optionally substituted heterocycle including at least one nitrogen, and an optionally substituted amine, or $R^3$ and $R^4$ can be joined together to form a bidentate ligand;
Z and Y are independently selected from the group consisting of O and S, provided at least one of Z and Y is S; and
$X^-$ is a counterion.

6. The compound of claim 2, wherein at least one of $R^1$ or $R^2$ is not alkyl or haloalkyl.

7. The compound of claim 2, wherein at least one of $R^3$ and $R^4$ is $NH_3$.

8. The compound of claim 2, wherein each of $R^3$ and $R^4$ is $NH_3$.

9. The compound of claim 2, wherein $R^3$ and $R^4$ are independently selected from the group consisting of ammonia and an optionally substituted amine, and are not joined together to form a bidentate ligand.

10. The compound of claim 2, wherein at least one of $R^1$ or $R^2$ is aryl optionally substituted.

11. The compound of claim 2, wherein at least one of $R^1$ or $R^2$ is not methyl or —$CF_3$.

12. The compound of claim 2, wherein at least one of $R^1$ is —$CH_3$ or —$CF_3$ and $R^2$ is aryl, optionally substituted.

13. The compound of claim 2, wherein each of $R^1$ and $R^2$ is aryl, optionally substituted.

14. The compound of claim 5, wherein Z is O and Y is S.

15. The compound of claim 5, wherein Z is S and Y is O.

16. The compound of claim 5, wherein each of Z and Y is S.

17. A pharmaceutical composition, comprising:
a compound as in claim 5; and
one or more pharmaceutically acceptable carriers, additives, and/or diluents.

* * * * *